US008352039B2

(12) United States Patent
Davis et al.

(10) Patent No.: US 8,352,039 B2
(45) Date of Patent: Jan. 8, 2013

(54) PROGRAMMING THERAPY DELIVERED BY IMPLANTABLE MEDICAL DEVICE

(75) Inventors: Jon P. Davis, St. Michael, MN (US); Steven M. Goetz, North Oaks, MN (US); Nathan A. Torgerson, Andover, MN (US); Wende L. Dewing, Edina, MN (US); Ashish Singal, Blaine, MN (US); Lynn A. Davenport, New Brighton, MN (US); Rajeev M. Sahasrabudhe, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 114 days.

(21) Appl. No.: 12/985,919

(22) Filed: Jan. 6, 2011

(65) Prior Publication Data
US 2011/0172737 A1 Jul. 14, 2011

Related U.S. Application Data

(60) Provisional application No. 61/293,393, filed on Jan. 8, 2010, provisional application No. 61/330,063, filed on Apr. 30, 2010.

(51) Int. Cl.
*A61N 1/00* (2006.01)
(52) U.S. Cl. .......................................................... 607/59
(58) Field of Classification Search ...................... 607/59
See application file for complete search history.

(56) References Cited

U.S. PATENT DOCUMENTS

| 5,431,691 | A | 7/1995 | Snell et al. |
|---|---|---|---|
| 5,513,645 | A | 5/1996 | Jacobson et al. |
| 5,833,623 | A | 11/1998 | Mann et al. |
| 5,938,690 | A | 8/1999 | Law et al. |
| 6,250,309 | B1 | 6/2001 | Krichen et al. |
| 6,308,102 | B1 | 10/2001 | Sieracki et al. |
| 6,480,743 | B1 | 11/2002 | Kirkpatrick et al. |
| 6,597,954 | B1 | 7/2003 | Piess et al. |
| 6,599,250 | B2 | 7/2003 | Webb et al. |
| 6,609,032 | B1 | 8/2003 | Woods et al. |
| 6,622,048 | B1 | 9/2003 | Mann et al. |
| 6,654,642 | B2 | 11/2003 | North et al. |
| 6,675,044 | B2 | 1/2004 | Chen |
| 6,845,267 | B2 * | 1/2005 | Harrison et al. .................. 607/3 |
| 7,181,286 | B2 | 2/2007 | Sieracki et al. |

(Continued)

OTHER PUBLICATIONS

Notification of Transmittal of the International Search Report and Written Opinion for corresponding patent application No. PCT/US2011/020526, mailed Jul. 5, 2011, 11 pages.

(Continued)

*Primary Examiner* — George Manuel
(74) *Attorney, Agent, or Firm* — Shumaker & Sieffert, PA

(57) ABSTRACT

This disclosure describes techniques for programming stimulation therapy programs according to therapy targets (e.g., symptoms or areas of pain) in a patient to which they are applied. Several programs can be programmed for each therapy target, stored on an implantable medical device, and retrieved later by a programmer to modify, edit, delete, create, and/or select a therapy program for each of the therapy targets. Each therapy target is independent from the other therapy targets, and a user can select or change a program under one therapy target without affecting programs under the other therapy targets. During programming, a user can specify parameters for each program applicable to only that program, and can specify parameters for each therapy target applicable to every program associated with that therapy target. The organization of programs into slots and the selection of a program in each slot may be manual or automated.

38 Claims, 23 Drawing Sheets

U.S. PATENT DOCUMENTS

| | | |
|---|---|---|
| 7,558,629 B2 | 7/2009 | Keimel et al. |
| 7,774,067 B2 | 8/2010 | Keacher et al. |
| 7,778,851 B2 | 8/2010 | Schoenberg et al. |
| 2001/0007950 A1 | 7/2001 | North et al. |
| 2002/0103505 A1 | 8/2002 | Thompson |
| 2002/0116036 A1 | 8/2002 | Daignault, Jr. et al. |
| 2002/0165437 A1 | 11/2002 | Chen |
| 2004/0143302 A1 | 7/2004 | Sieracki et al. |
| 2004/0199217 A1 | 10/2004 | Lee et al. |
| 2005/0085738 A1 | 4/2005 | Stahmann et al. |
| 2005/0113887 A1 | 5/2005 | Bauhahn et al. |
| 2005/0209645 A1 | 9/2005 | Heruth et al. |
| 2006/0235472 A1 | 10/2006 | Goetz et al. |
| 2006/0241720 A1 | 10/2006 | Woods et al. |
| 2007/0135690 A1 | 6/2007 | Nicholl |
| 2007/0150026 A1 | 6/2007 | Bourget et al. |
| 2007/0244511 A1 | 10/2007 | Weizman et al. |
| 2007/0244519 A1 | 10/2007 | Keacher et al. |
| 2007/0249968 A1 | 10/2007 | Miesel et al. |
| 2007/0299317 A1 | 12/2007 | Hoyme et al. |
| 2008/0071581 A1 | 3/2008 | Luttrell |
| 2009/0112289 A1 | 4/2009 | Lee et al. |
| 2009/0281596 A1 | 11/2009 | King et al. |
| 2010/0076787 A1 | 3/2010 | Naylor et al. |
| 2010/0130831 A1 | 5/2010 | Sato et al. |

OTHER PUBLICATIONS

U.S. Appl. No. 12/986,683, filed Jan. 7, 2011, Davis et al.

U.S. Appl. No. 12/771,652, filed Apr. 30, 2010, Davis et al.

AspectMD TM Electronic Medical Record, Lightstream Solutions, http://www.lightstreamsolutions.com/aspectmd.html, downloaded Mar. 2011 (2 pgs.).

EMR eClinicalWorks, http://www.eclinicalworks.com/code.php, downloaded Mar. 2011 (3 pgs.).

InSync III Cardiac Resynchronization Therapy Pacemaker (CRT-P), http://www.medtronic.com/physician/brady/enpulse/quicklook.html, downloaded Mar. 2011 (3 pgs.).

Specialty EMR, Softwares Medical Record System, http://www.omnimd.com/html/emrsscreens.html, downloaded Mar. 2011 (2 pgs.).

Speciality EMR, Software for Clinical Practices in US, http://www.omnimd.com/html/EMRS.html, downloaded Mar. 2011 (2 pgs.).

* cited by examiner

PROGRAMMING THERAPY DELIVERED BY IMPLANTABLE MEDICAL DEVICE

This application claims the benefit of U.S. Provisional Application No. 61/293,393, entitled "PROGRAMMING THERAPY DELIVERED BY IMPLANTABLE MEDICAL DEVICE," filed on Jan. 8, 2010; and U.S. Provisional Application No. 61/330,063, entitled "PROGRAMMING THERAPY DELIVERED BY IMPLANTABLE MEDICAL DEVICE," filed on Apr. 30, 2010, the entire contents of each of these applications being incorporated herein by reference.

TECHNICAL FIELD

The disclosure relates to medical devices and, more particularly, to programming of therapy delivered by a medical device.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify parameter values in the form of pulse amplitude, pulse width and pulse rate, for example. Parameter values may also include an electrode configuration specifying, for example, a selected set of electrodes for delivery of stimulation and polarities for the electrodes. A set of parameter values may be referred to as a stimulation program. A program group may include multiple programs. Multiple programs in a program group may be delivered on a simultaneous, time-interleaved, or overlapping basis.

SUMMARY

Generally, this disclosure describes techniques for organizing stimulation therapy programs such that several programs can be active simultaneously, and changing or replacing one of the programs does not affect the other programs. The active programs may be delivered on a simultaneous, time-interleaved, or overlapping basis. The programs may be created and manipulated utilizing a graphical view of electrodes used to deliver electrical stimulation therapy according to the active programs, and one or more images displaying the different therapy targets to which the electrodes are to deliver electrical stimulation therapy.

The active stimulation programs may be defined by programs selected for a set of program slots, where each slot may designate selection of one of a plurality of alternative programs for the slot. The alternative programs for a given slot may represent different therapy targets for the slot, where the therapy targets in a slot represent the same symptom or area of pain in a patient. In some examples, each slot may have a different therapy target, such that the therapy applied by a selected program in each slot targets a different symptom or area of pain. In addition, in some cases, each slot may be individually controlled, e.g., independently of other slots. A pain map may be associated with each individual slot. Paresthesia maps may also be associated with each therapy option in a given slot. In some examples, the pain map and paresthesia map may be analyzed to evaluate efficacy of therapy for a given slot or set of slots. In some examples, activation of different programs within the slots may be tracked and the historical information may be stored and subsequently accessed or displayed to a user for decision-making regarding future parameter adjustments.

In one example, the disclosure is directed to a device comprising at least one processor configured to perform at least one of organizing a plurality of electrical stimulation therapy programs by therapy targets in a patient, wherein two or more of the electrical stimulation therapy programs are associated with each of two or more therapy targets, and selecting one of the electrical stimulation therapy programs for each of the therapy targets, wherein selection of one of the electrical stimulation therapy programs for one of the therapy targets is independent of selection of one of the electrical stimulation therapy programs for another of the therapy targets, and wherein the selected electrical stimulation therapy programs are applied to the patient by an implantable electrical stimulator.

In another example, the disclosure is directed to a method comprising organizing a plurality of electrical stimulation therapy programs by therapy targets in a patient, wherein two or more electrical stimulation therapy programs are associated with each of two or more therapy targets, and selecting one of the electrical stimulation therapy programs for each of the therapy targets, wherein selection of one of the electrical stimulation therapy programs for one of the therapy targets is independent of selection of one of the electrical stimulation therapy programs for another of the therapy targets, and wherein the selected electrical stimulation therapy programs are applied to the patient by an implantable electrical stimulator.

In another example, the disclosure is directed to a system comprising means for organizing a plurality of electrical stimulation therapy programs by therapy targets in a patient, wherein two or more electrical stimulation therapy programs are associated with each of two or more therapy targets, and means for selecting one of the electrical stimulation therapy programs for each of the therapy targets, wherein selection of one of the electrical stimulation therapy programs for one of the therapy targets is independent of selection of one of the electrical stimulation therapy programs for another of the therapy targets, and wherein the selected electrical stimulation therapy programs are applied to the patient by an implantable electrical stimulator.

In another example, the disclosure is directed to a computer-readable medium comprising instructions that, upon execution, cause a processor to organize a plurality of electrical stimulation therapy programs by therapy targets in a patient, wherein two or more electrical stimulation therapy programs are associated with each of two or more therapy targets, and select one of the electrical stimulation therapy programs for each of the therapy targets, wherein selection of one of the electrical stimulation therapy programs for one of the therapy targets is independent of selection of one of the electrical stimulation therapy programs for another of the therapy targets, and wherein the selected electrical stimulation therapy programs are applied to the patient by an implantable electrical stimulator.

In another example, the disclosure is directed to a programmer comprising a communication module that transfers a plurality of electrical stimulation therapy programs from a device, wherein the plurality of programs are organized by therapy targets in a patient, wherein two or more electrical stimulation therapy programs are associated with each of two or more symptoms of a patient, and a processor that controls selection of one of the electrical stimulation therapy program for each of the therapy targets in response to the user input, wherein selection of one of the electrical stimulation therapy programs for one of the therapy targets is independent of selection of one of the electrical stimulation therapy programs for another of the therapy targets, and wherein the selected electrical stimulation therapy programs are applied to the patient by the implantable electrical stimulator.

In another example, the disclosure is directed to a method comprising transferring a plurality of electrical stimulation therapy programs from a device, wherein the plurality of programs are organized by therapy targets in a patient, wherein two or more of the electrical stimulation therapy programs are associated with each of two or more therapy targets, and selecting one of the electrical stimulation therapy programs for each of the therapy targets, wherein selection of one of the electrical stimulation therapy programs for one of the therapy targets is independent of selection of one of the electrical stimulation therapy programs for another of the therapy targets, and wherein the selected electrical stimulation therapy programs are applied to the patient by an implantable electrical stimulator.

In another example, the disclosure is directed to a system comprising means for a plurality of electrical stimulation therapy programs from a device, wherein the plurality of programs are organized by therapy targets in a patient, wherein two or more of the electrical stimulation therapy programs are associated with each of two or more therapy targets, and means for selecting one of the electrical stimulation therapy programs for each of the therapy targets in response to the user input, wherein selection of one of the electrical stimulation therapy programs for one of the therapy targets is independent of selection of one of the electrical stimulation therapy programs for another of the therapy targets, and wherein the selected electrical stimulation therapy programs are applied to the patient by an implantable electrical stimulator.

In another example, the disclosure is directed to a computer-readable medium comprising instructions that, upon execution, cause a processor to transfer a plurality of electrical stimulation therapy programs from a device, wherein the plurality of programs are organized by therapy targets in a patient, wherein two or more of the electrical stimulation therapy programs are associated with each of two or more therapy targets, and select one of the electrical stimulation therapy programs for each of the therapy targets, wherein selection of one of the electrical stimulation therapy programs for one of the therapy targets is independent of selection of one of the electrical stimulation therapy programs for another of the therapy targets, and wherein the selected electrical stimulation therapy programs are applied to the patient by an implantable electrical stimulator.

The details of one or more aspects of the disclosure are set forth in the accompanying drawings and the description below. Other features, objects, and advantages will be apparent from the description and drawings, and from the claims.

DETAILED DESCRIPTION

The techniques described in this disclosure may provide a user with the ability to define stimulation therapy programs that have various therapy targets, which may be, for example, symptoms or areas of pain, such as selected regions in the body, from which a user can select a desired set of active programs to be applied. The disclosure describes various techniques for creating, adjusting, organizing, and evaluating these programs to provide great flexibility and dynamicity in selecting and changing therapy programs. A set of program slots may be defined and organized, where each slot may include one or more programs that form therapy options for the slot, and each slot may have a different therapy target (e.g., symptom or area of pain). One program may be selected from each slot, where the selection of a program in one slot is independent of the programs selected in other slots. A user may utilize a device (e.g., a programmer) to define and organize the stimulation therapy programs for a patient and store them on an implantable medical device (IMD) implanted in the corresponding patient. In one example, the user may be a clinician or physician and may define the stimulation therapy programs, activate stimulation therapy programs, and/or modify the stimulation therapy programs. In another example, the user may be the patient and may utilize a patient programmer to change some parameters or change the active stimulation therapy programs. A user, such as a clinician or physician, may utilize a programmer to define parameters and/or programs that a user may be capable of modifying using a patient programmer.

As noted above, a user may utilize a programmer to define stimulation therapy programs for different therapy targets. In one example, the user may utilize the programmer to further organize the therapy programs in different slots according to therapy targets. Additionally, the user may utilize the programmer to select a stimulation therapy program within each slot, where the selected programs are applied to the patient by an IMD. In some examples, a device may automatically perform the organizing of the therapy programs into the different slots and/or the selection of the programs. The device may be a programmer (e.g., clinician or patient programmer) or the IMD. The automated organization and/or selection of the stimulation therapy programs may be based on factors such as, for example, patient data, patient condition, and/or sensed signals, as described in more detail below.

Figure 1:
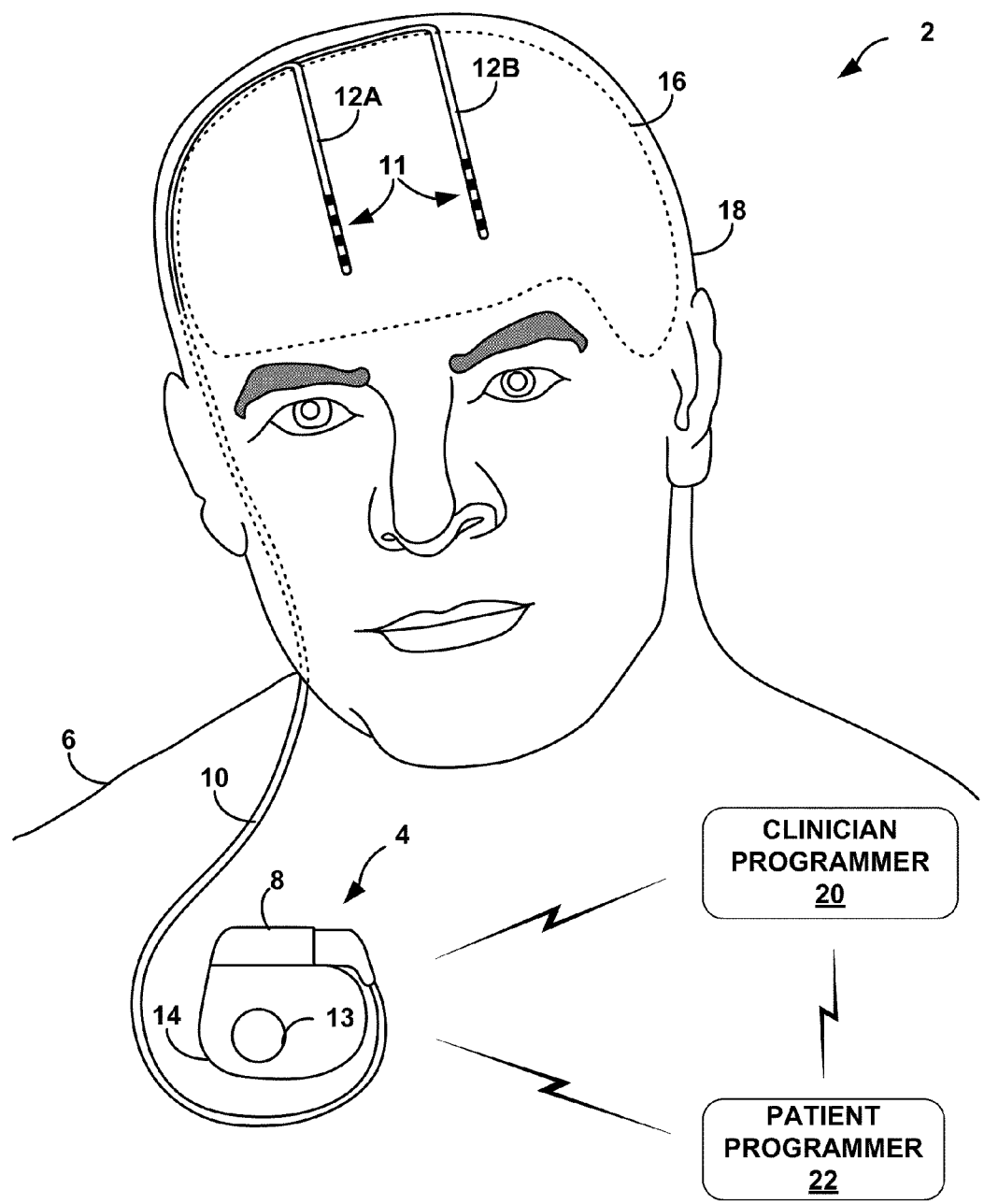
FIG. 1 is a conceptual diagram illustrating an example therapy system that includes an implantable electrical stimulator.

FIG. 1 is a conceptual diagram illustrating an example therapy system 2 including an implantable electrical stimulator 4 that may be used to deliver stimulation therapy to patient 6. Patient 6 ordinarily, but not necessarily, will be a human. Generally, therapy system 2 includes implantable electrical stimulator 4 that delivers electrical stimulation to patient 6 via one or more implantable electrodes 11. The implantable electrodes 11 may be deployed on one or more implantable medical leads, such as implantable medical lead 10, and in some cases on a can electrode. The electrical stimulation may be in the form of controlled current or voltage pulses or substantially continuous waveforms. Various parameters of the pulses or waveforms may be defined by one or more stimulation programs. The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads with a patch electrode or other indifferent electrode attached externally to serve as the can or case. One or more of the electrodes may be located on a housing 14, i.e., "can" or "case," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, e.g., a current waveform or current pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, twelve, sixteen, or more electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

FIG. 1 further depicts a housing, or can, electrode 13. Housing electrode 13 may be formed integrally with an outer surface of hermetically-sealed housing 14 of implantable stimulator 4, also referred to in this disclosure as implantable medical device (IMD) 4, or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, one side of housing 14, a portion of the housing 14, or multiple portions of housing 14. In other examples, electrode 13 may be formed by an electrode on a dedicated short lead extending from housing 14. As a further alternative, housing electrode 13 could be provided on a proximal portion of one of the leads carrying electrodes 11. The proximal portion may be closely adjacent to housing 14, e.g., at or near a point at which lead 10 is coupled to the housing, such as adjacent to a lead connection header 8 of the housing. In another example, a patch electrode or other indifferent electrode may be attached externally to serve as the can or case.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to implantable stimulator 4 via a common lead extension or via separate lead extensions.

A proximal end of lead 10 may be both electrically and mechanically coupled to header 8 on implantable stimulator 4, either directly or indirectly via a lead extension. Conductors in the lead body may electrically connect stimulation electrodes located on lead segments 12 to implantable stimulator 4. Lead 10 traverses from the implant site of implantable stimulator 4 along the neck of patient 6 to cranium 18 of patient 6 to access brain 16. Lead segments 12A and 12B are implanted within the right and left hemispheres, respectively, in order to deliver electrical stimulation to one or more regions of brain 16, which may be selected based on the patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder, and movement disorders, such as Parkinson's disease, spasticity, epilepsy, and dystonia. DBS may be also useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex or near the occipital nerves of brain 16 in order to reduce or eliminate migraine headaches afflicting patient 6. However, the target therapy delivery site may depend upon the patient condition or disorder being treated. While the examples of FIG. 1 shows lead segments 12A and 12B implanted in a brain, in other examples, lead segments 12A and 12B may be implanted in other regions or organs of patient's body.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry, Bluetooth®, and other wireless or wired communication protocols) with implantable stimulator 4 to transfer programs and, optionally, transfer operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4. In some examples, patient programmer 22 may serve as the clinician programmer.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop, or adjust electrical stimulation therapy. In particular, patient programmer 22 may permit patient 6 to adjust stimulation parameters of a program such as duration, current or voltage amplitude, pulse width and pulse rate. Patient 6 may also select a program, e.g., from among a plurality of stored programs, as the present program to control delivery of stimulation by implantable stimulator 4.

Clinician programmer 20 and/or patient programmer 22 may be used to graphically define desired stimulation field(s) within zones on or adjacent to one or more leads, and generate the stimulation required to create the stimulation field. In particular, clinician programmer 20 and/or patient programmer 22 may be used for translating one or more user input stimulation zones into a set of electrodes for delivering electrical stimulation therapy to a patient, determining the variable electrical stimulation contributions of each electrode to the zone, and determining amplitudes of electrical stimulation when using zone-based programming. Clinician programmer 20 and/or patient programmer 22 may also be used for graphically representing the stimulation zone and receiving input from a user that manipulates the shape and position of the zone. In one example, clinician programmer 20 may be used to define and store one or more programs to target a specific therapy target with different parameters. The programs may be grouped according to the therapy targets of the therapy, e.g., back or right leg, etc., so that a user may select the program most appropriate for the patient, as will be discussed in more detail below.

In one example, patient programmer 22 may be used by a clinician to program therapy, as he/she would be able to do on a clinician programmer 20. The clinician may be able to "unlock" the patient programmer 22 to be able to use it as a clinician programmer. In one example, the patient may be able to adjust some therapy options and parameters using patient programmer 22. In one example, a clinician may control therapy options and parameters that the user can adjust, i.e., control access permissions for patient programmer 22. Patient programmer 22 may allow patient 6 to select or change the active program in each of the active slots. Example aspects of patient programmer 22 will be described in more detail below.

In some examples, implantable stimulator 4 delivers stimulation according to programs organized in slots. Each slot may include one or more programs that target a therapy target. A therapy target may be a basis for segregating therapy configuration options. Some examples of therapy targets may include symptom, area of pain, anatomical target of the lead, anatomical target of the therapy, or other basis for segregating therapy configuration options. Each program may define values for each of a plurality of therapy parameters, such as values for each of current or voltage amplitude, pulse width, pulse shape, pulse rate and electrode configuration (e.g., electrode combination and polarity). In one example, the IMD may be capable of sensing, and the parameters may also include one or more sensing-related parameters such as, for example, gains, filter bandwidths, and sampling rates. Implantable stimulator 4 may interleave pulses or other signals according to the different active programs of program slots, e.g., cycle through the programs, to simultaneously treat different therapy targets (e.g., symptoms or pain areas), or provide a combined therapeutic effect. In such examples, clinician programmer 20 or patient programmer 22 may be used to create programs, and organize the programs into program slots. Patient programmer 22 may be used to adjust stimulation parameters of one or more programs of a program slot, and select a program from among a plurality of programs in each slot, as the current programs to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art or other standard communication protocols such as, for example, Bluetooth®. Clinician programmer 20 and patient programmer 22 may also communicate with each other using any of a variety of wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Generally, system 2 delivers stimulation therapy to patient 6 in the form of constant current or voltage waveforms or constant current or voltage pulses. The shapes of the pulses may vary according to different design objectives. In the case of current-based stimulation, implantable stimulator 4 regulates current that is sourced or sunk by one or more electrodes, referred to as regulated electrodes. In some examples, one or more of the electrodes may be unregulated. In some configurations, either the housing electrode or a lead electrode may be the unregulated electrode.

A source current may refer to a positive current that flows out of an electrode, e.g., from a regulated current source via a regulated current path to surrounding tissue, or from a reference voltage via an unregulated current path. A sink current may refer to a negative current that flows into an electrode, e.g. from surrounding tissue and is sunk by a regulated current sink via a regulated current path or by a reference voltage via an unregulated current path. Regulated source currents may sum to produce a greater overall source current. Regulated sink currents may sum to produce a greater overall sink current. Regulated source and regulated sink currents may partially or entirely cancel one another, producing a net difference in the form of a net source current or sink current. An unregulated current path can source or sink current approximately equal to this net difference.

Figure 2:
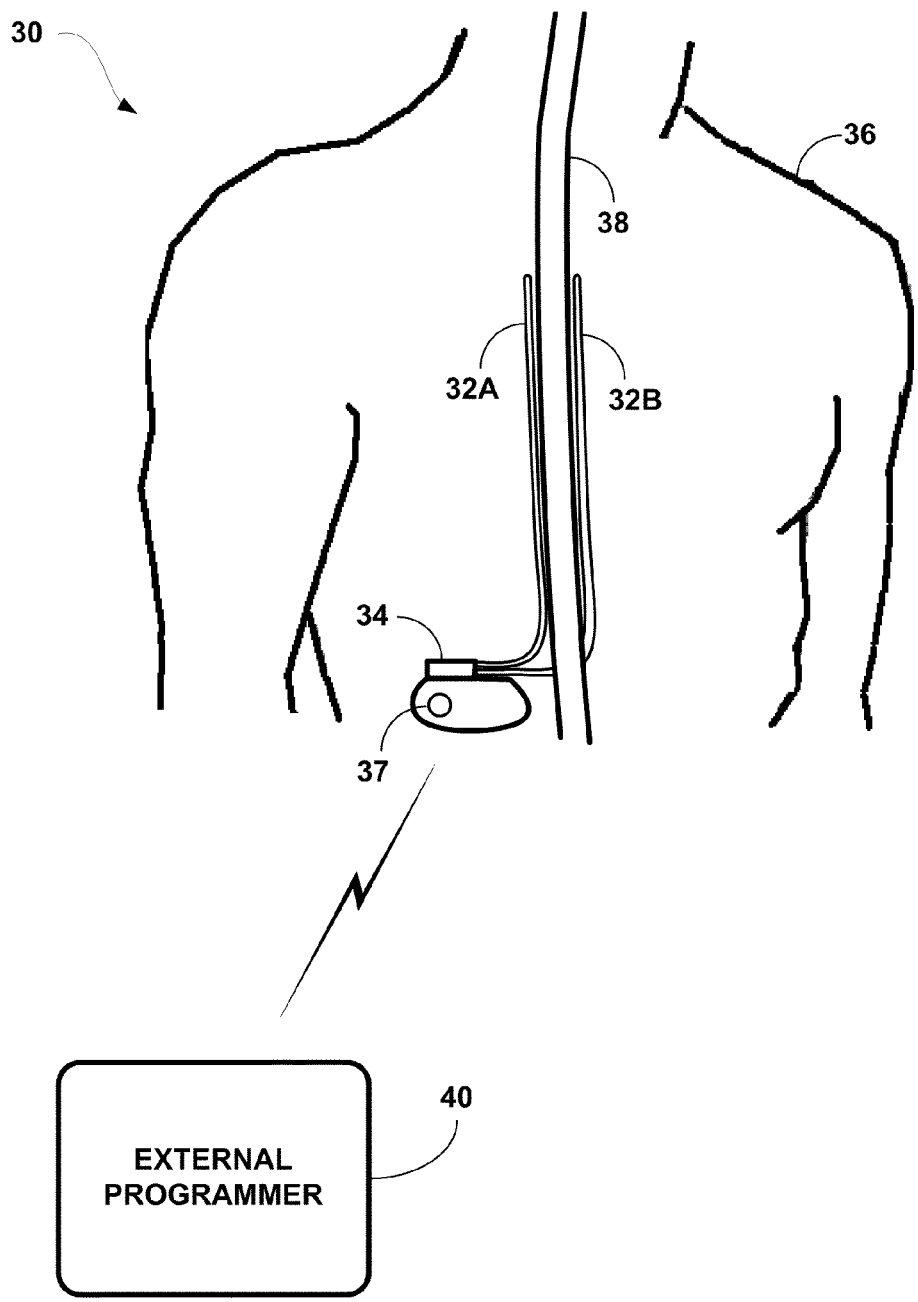
FIG. 2 is a conceptual diagram illustrating another example therapy system that includes an implantable electrical stimulator.

FIG. 2 is a conceptual diagram illustrating system 30 that delivers stimulation therapy to spinal cord 38 of patient 36. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from implantable stimulator 34 to spinal cord 38 via one or more electrodes (not shown) carried by, i.e., located on, implantable medical leads 32A and 32B (collectively "leads 32") as well as the housing of implantable stimulator 34, e.g., housing electrode 37. System 30 and, more particularly, implantable stimulator 34 may operate in a manner similar to implantable stimulator 4 (FIG. 1). That is, in a current-based example, implantable stimulator 34 delivers controlled current stimulation pulses or waveforms to patient 36 via one or more regulated stimulation electrodes. Alternatively, implantable stimulator 34 may be configured to deliver constant voltage pulses. As mentioned above, in some examples, one or more of the electrodes may be unregulated.

In the example of FIG. 2, the distal ends of leads 32 carry electrodes that are placed adjacent to the target tissue of spinal cord 38. The proximal ends of leads 32 may be both electrically and mechanically coupled to implantable stimulator 34 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described in this disclosure with respect to implantable stimulator 34 and implantable leads 32 having ring electrodes for purposes of illustration. However, other types of electrodes may be used.

Stimulator 34 may be implanted in patient 36 at a location minimally noticeable to the patient. For SCS, stimulator 34 may be located in the lower abdomen, lower back, or other location to secure the stimulator. Leads 32 may be tunneled from stimulator 34 through tissue to reach the target tissue adjacent to spinal cord 38 for stimulation delivery. At the distal ends of leads 32 are one or more electrodes (not shown) that transfer the stimulation pulses from the lead to the tissue substantially simultaneously with stimulation pulses. Some of the electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar or multi-polar electrode configurations.

The stimulation pulses may be delivered using various electrode arrangements such as unipolar arrangements, bipolar arrangements or multipolar arrangements. A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sinks current. A multipolar stimulation arrangement generally refers to the use of more than one anode on a lead that each source current and one or more cathodes on the same lead or another lead that sink current, or the use of one anode on a lead that sources current and multiple cathodes on the same lead or another lead that sink current. A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver electrical stimulation in accordance with techniques described in this disclosure.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by implantable stimulator 34 may take the form of stimulation pulses or continuous stimulation waveforms, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 34 perceives the interruption of pain signals as a reduction in pain and, therefore, efficacious therapy.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry.

In some cases, external programmer 40 may be characterized as a physician or clinician programmer, such as clinician programmer 20 (FIG. 1), if it is primarily intended for use by a physician or clinician. In other cases, external programmer 40 may be characterized as a patient programmer, such as patient programmer 22 (FIG. 1), if it is primarily intended for use by a patient. In general, a physician or clinician programmer may support selection, generation, and modification of programs by a clinician for use by stimulator 34, whereas a patient programmer may support adjustment and selection of such programs by a patient during ordinary use, and may be limited to certain operations as specified by a clinician, for example.

Whether programmer 40 is configured for clinician or patient use, programmer 40 may communicate to implantable stimulator 34 or any other computing device via wireless communication. Programmer 40, for example, may communicate via wireless communication with implantable stimulator 34 using radio frequency (RF) telemetry techniques known in the art or other communication standards such as, for example, Bluetooth®. In one example, programmer 40 may also communicate with an external stimulator used for screening therapy prior to implant of a chronic stimulation system. In another example, programmer 40 may be a clinician programmer and may communicate with a patient programmer to store therapy parameter settings or other configurations, which the patient programmer may subsequently communication to the IMD. Programmer 40 may also communicate with another programmer or computing device via a wired or wireless connection using any of a variety of local wireless communication techniques, such as RF communication according to the 802.11 or Bluetooth® specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 34 and other programming devices via remote telemetry techniques known in the art, communicating via a local area network (LAN), wide area network (WAN), public switched telephone network (PSTN), or cellular telephone network, for example.

Programming of stimulator 34 may also include graphically defining a desired stimulation field(s) within zones on or adjacent to one or more leads or electrodes, and generating, via a programmer, the current stimulation required to create the stimulation field. Programming of stimulator 34 may also include translating one or more user input stimulation zones into a set of electrodes for delivering electrical stimulation therapy to a patient, and a set of parameters such as pulse current amplitudes associated with such electrodes. Programming may further include manipulating the shape and position of the zone, including behaviors of the zone while moving and when colliding with other zones or system interlocks. As the stimulation zone is sized, moved, or shaped, the programmer may automatically compute updated electrode selections and parameters for delivery of stimulation indicated by the stimulation zone.

Although the disclosure generally refers to implantable stimulators for purposes of illustrations, techniques described in this disclosure also may be used with respect to therapy targets (e.g., symptoms, anatomical regions, or pain areas) targeted by other types of implantable medical devices, including implantable fluid delivery devices, such as insulin pumps, intra-thecal drug delivery pumps, or other devices that deliver medication or other fluids via one or more fluid delivery elements such as catheters. Such devices may provide fluid delivery therapy for chronic pain, diabetes, or any of a variety of other disorders. In each case, the device may include one or more therapy delivery elements such as one or more catheters implanted within a therapy region. In some cases, a pump may be fully implantable or may be an external device coupled to one or more percutaneously implanted catheters that extend into a therapy region. Accordingly, description of implantable stimulators is provided for purposes of illustration and should not be considered limiting of the techniques as broadly described in this disclosure.

Figure 3:
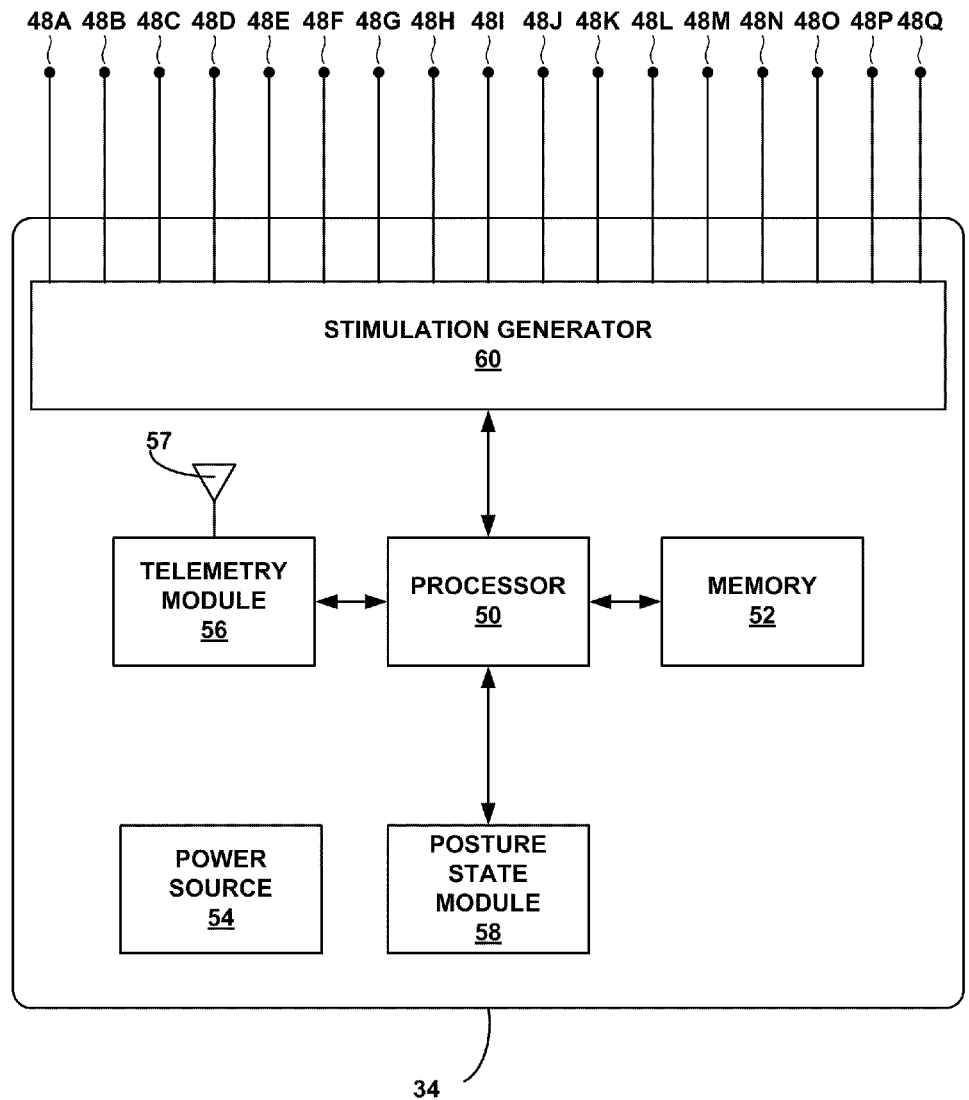
FIG. 3 is a block diagram illustrating various example components of an implantable electrical stimulator.

FIG. 3 is a block diagram illustrating various components of an example implantable stimulator 34. Although the components shown in FIG. 3 are described in reference to implantable stimulator 34, the components may also be included within implantable stimulator 4 shown in FIG. 1 and used within system 2. In the example of FIG. 3, implantable stimulator 34 includes processor 50, memory 52, power source 54, telemetry module 56, antenna 57, posture state module 58, and a stimulation generator 60.

Implantable stimulator 34 is also shown in FIG. 3 coupled to electrodes 48A-Q (collectively "electrodes 48"). Electrodes 48A-48P are implantable and may be deployed on one or more implantable leads. With respect to FIG. 1, lead segments 12A and 12B may carry electrodes 48A-H and electrodes 48I-P, respectively. In some cases, one or more additional electrodes may be located on or within the housing of implantable stimulator 34, e.g., to provide a common or ground electrode or a housing anode. With respect to FIG. 2, leads 32A and 32B may carry electrodes 48A-H and electrodes 48I-P, respectively. In the examples of FIGS. 1 and 2, a lead or lead segment carries eight electrodes to provide an 2×8 electrode configuration (two leads with 8 electrodes each), providing a total of sixteen different electrodes. The leads may be detachable from a housing associated with implantable stimulator 34, or be fixed to such a housing. In general, electrodes 48A-48Q may be referred to below as electrodes 48 for conciseness.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), or other configurations. Different electrodes are selected to form electrode combinations. Polarities are assigned to the selected electrodes to form electrode configurations.

Electrode 48Q represents one or more electrodes that may be carried on a housing, i.e., can, of implantable stimulator 34. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 34, such as stimulation generator 60, processor 50, memory 52, telemetry module 56, and power source 54.

Housing electrode 48Q may be configured for use as an anode to source current substantially simultaneously with current sourced by one or more other electrodes 48A-48P to form a unipolar or omnipolar arrangement. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q. Any of a variety of electrode arrangements such as unipolar, bipolar, multipolar, or omnipolar arrangements may be used to deliver stimulation. Accordingly, discussion of particular arrangements is provided for purposes of illustration, but should not be considered limiting of the techniques broadly described in this disclosure.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

Posture state module 58 allows IMD 34 to sense the patient posture state, e.g., posture, activity or any other static position or motion of the patient. In the example of FIG. 3, posture state module 58 includes one or more accelerometers, such as three-axis accelerometers, capable of detecting static orientation or vectors in three-dimensions (e.g., x, y, z coordinate vectors). Example accelerometers may include a micro-electro-mechanical systems (MEMS)-based accelerometer. In other examples, posture state module 58 may alternatively or additionally include one or more gyroscopes, piezoelectric crystals, pressure transducers or other sensors to sense the posture state of the patient. Posture sensor data generated by posture state module 58 and processor 50 may correspond to an activity and/or posture undertaken by the patient or a gross level of physical activity, e.g., activity counts based on footfalls or the like. In one example, posture sensor data may detect a patient posture, such as, for example, upright, lying left, lying right, lying down, lying up, reclining, etc.

In accordance with the techniques described in this disclosure, information stored on the memory 52 may include information regarding therapy that the patient 6 had previously received or information regarding a current therapy. Storing such information may be useful for subsequent therapy such that, for example, a clinician may retrieve the stored information to determine the therapy applied to the patient during a previous therapy session or therapy programs defined in a previous clinic session, in accordance with this disclosure. The information stored in the memory 52 may be, for example, programs associated with different therapy targets (e.g., symptoms and/or pain areas targeted by therapy defined by the programs), where each therapy target has one or more programs associated with it.

As an example, for a certain patient, the therapy targets may be the back and right leg. There may be one or more programs that define therapies associated with the back, where each program may have certain variations for at least some of the program parameters. Similarly, there may be one or more programs that define therapies associated with the right leg, where each program may have certain variations for at least some of the program parameters. The programs associated with a therapy target (e.g., symptom and/or pain area) may be organized into a slot for that therapy target, e.g., the programs that define therapies for the back may be organized into a slot for the back, and programs that define therapies for the right leg may be organized into a slot for the right leg. In some examples, the slots may be configured so that multiple slots may provide therapy to a single therapy target. In yet another example, the slots may be configured so that multiple therapy targets may be targeted by a single slot. In another example, information stored in memory 52 may be additionally or alternatively stored in the patient programmer.

A user may select one program from each slot, or change the selected program from a given slot, independently from programs selected in other slots. Each program in a given slot targets the therapy target (e.g., pain area, anatomical target, or other symptom associated with the slot), and selection of a program in one slot may be done by the patient, the clinician, or automatically. In one example, the patient may change a program for one therapy target based on the comfort level felt during application of a therapy. In another example, a program may be automatically changed/selected based on a sensed posture of the patient. For example, a slot associated with the back may include a program defining therapy to be applied when the patient is standing upright, another program defining therapy to be applied when the patient is lying down, and another program defining therapy to be applied when the patient is reclining. In another example, slot contents may be changed on a time schedule, such that during a trial period the patient receives a randomized sequence of therapy options, each for at least a minimum duration of time. In yet another example, slot contents may be changed during the day, where different therapy options may be applied at different times of the day, or different therapy options may be applied based on an amount of activity of the patient, or the like.

In one example, posture responsive stimulation (PRS) may be enabled for at least some of the slots. Generally, PRS involves adjusting stimulation in response to posture, e.g., adjusting parameters of a program, such as, for example, changing amplitude of a active program, when the patient changes posture, or selecting different programs with several different parameters (e.g., pulse width, amplitude, pulse rate) for different postures.

In an example, programs in a certain slot may correspond to posture-dependent therapies for the therapy target (e.g., symptom or pain area) associated with the slot. Some therapy targets may not have posture-responsive adjustments, and other therapy targets may have different posture-responsive adjustments than other therapy targets. For example, in one slot, one program may correspond to the upright posture and another program to the lying down posture. In another slot, one program may correspond to the upright posture and another program to the reclining posture. In yet another slot, posture may not be a factor in selecting a program. In one example, a program may correspond to more than one posture, e.g., the same program may be applied for upright and lying down postures with a variation in a single parameter such as, for example, amplitude applied on transition between postures. In an example, PRS may be variable per slot and/or per program.

The programs associated with the therapy targets (e.g., symptoms and/or pain areas) may be set up and organized using a programmer, such as clinician programmer 20, and downloaded into the implantable stimulator 34 by wireless telemetry. As an example, the programs may be organized and set up during an in-clinic programming session. In some examples, the clinician may request that the patient sit, stand, lie down, or take any posture or activity applicable to the therapy target when programming the therapy programs for that area. In another example, the patient may change parameters for certain programs based on different postures. The different postures may be detected, e.g., automatically, and the corresponding changes may be recorded, e.g., automatically, and used in programming posture-responsive programs. In one example, the patient may change parameters, e.g., amplitude, based on different postures for programs in one slot, and the changes may then be used for automated PRS for the programs in that slot.

In one example, the change may be accomplished in an absolute sense, for example, a transition from upright position to reclining position may result in modification of a parameter of the active program in a slot, for example, decreasing the amplitude by 3.0 volts, 3.0 mA, or another absolute measure. In another example, the change may be accomplished in a relative fashion, for example, a transition from upright position to reclining position may result in the active program in a slot decreasing parameter, for example, the amplitude by 20%. The programs may be stored in the implantable medical device to ensure that the programs for the associated patient may be accessed by an external programmer whenever the patient is present, e.g., whenever the patient visits a clinic for a programming session or other evaluation. In one example, the patient may view the active slots and programs within the slot, and adjust active programs and parameters using a patient programmer, e.g., patient programmer 22 (FIG. 1).

The programs for each therapy target (e.g., symptom or pain area) may be organized together, e.g., in a drop down menu or column of a table, from which a user may select a desired program for the therapy target. The therapy target may be defined by a program slot, where a user may selectively fill that slot with one of a plurality of alternative programs designated as therapy options for the slot. The programs forming the therapy options for a given slot may be defined by a clinician during a visit, by a patient at home using his/her patient controller, or automatically by the system based on algorithmic variations of a selected starting option. Generating programs automatically is generally described in U.S. Pat. No. 7,774,067, entitled "AUTOGENERATION OF NEUROSTIMULATION THERAPY PROGRAM GROUPS," issued Aug. 10, 2010, the entire content of which is incorporated herein by reference.

In one example, configurations of slot or program parameters may be performed automatically based on an anatomical target or disease state associated with a given slot. For example, slots associated with targets that are not susceptible to postural variation, e.g., peripheral nerves, may have their posture response capability automatically disabled. The therapy target may be any of several anatomical regions of patient corresponding to areas of pain for the patient, for which therapy is needed to relieve pain.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 34, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program for each therapy target, processor 50 may control stimulation generator 60 to deliver stimulation according to the selected programs. As mentioned previously, each program may specify a set of stimulation parameters relating to a therapy target. The parameters may include, for example, amplitude, pulse width and pulse rate, if applicable. For a continuous waveform, parameters may include amplitude and frequency, for example. In addition, each program may specify a particular electrode configuration for delivery of stimulation, e.g., in terms of selected electrode combination, and the polarities and regulated/unregulated status of the electrodes in the combination. The electrode combination may specify particular electrodes in a single array or multiple arrays, and on a single lead or among multiple leads.

Stimulation generator 60 is electrically coupled to electrodes 48A-P via conductors of the respective lead, such as lead 12 in FIG. 1 or leads 32 in FIG. 2, in implementations in which electrodes 48A-P are carried by, located on, leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 3). A housing electrode 48Q may be configured as a regulated or unregulated electrode to form an electrode configuration in conjunction with one or more of electrodes 48A-48P located on leads of the IMD.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

Stimulation generator 60 may be configured to deliver stimulation using one or more of electrodes 48A-P as stimulation electrodes. The anodes on the lead(s) and the housing may be used to deliver stimulation in conjunction with one or more cathodes on the lead(s). As one illustration, an electrode combination selected for delivery of stimulation current may comprise an anode on the IMD housing, and anode on a lead, and a cathode on the same lead or a different lead. In other examples, the electrode combination may include multiple anodes and/or multiple cathodes on one or more leads in conjunction with at least one anode on the IMD housing.

Telemetry module 56 may include a radio frequency (RF) transceiver to permit bi-directional communication between implantable stimulator 34 and each of clinician programmer 20 and patient programmer 22. In one example, telemetry module 56 may utilize other communication protocols and a corresponding transceiver, for example, a Bluetooth® transceiver for telemetry using the Bluetooth® protocol. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 34 or take the form of a circuit trace on the circuit board. In this way, telemetry module 56 may permit communication with clinician programmer 20 and patient programmer 22 in FIG. 1 or external programmer 40 in FIG. 2, to receive, for example, new programs or adjustments to programs. Telemetry module 56 may also permit communication with clinician programmer 20 to send, for example, programs associated with the different therapy targets so that a programmer may set up stimulation therapy programs accordingly.

Power source 54 may be a non-rechargeable primary cell battery or a rechargeable battery and may be coupled to power circuitry. However, the disclosure is not limited to embodiments in which the power source is a battery. In another example, as an example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within stimulator 4. In some examples, power requirements may be small enough to allow stimulator 4 to utilize patient motion at least in part and implement a kinetic energy-scavenging device to trickle charge a rechargeable battery. A voltage regulator may generate one or more regulated voltages using the battery power.

Figure 4:
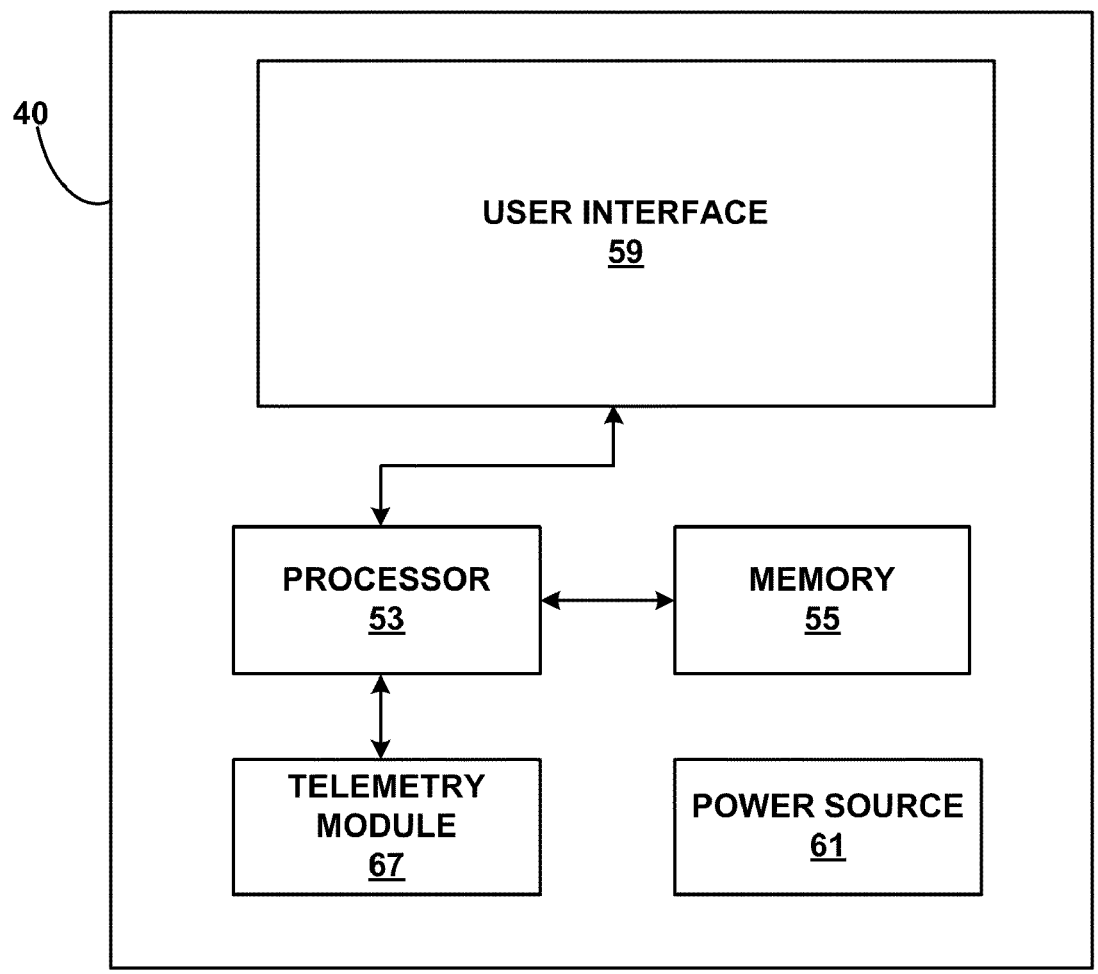
FIG. 4 is a block diagram illustrating various example components of an external programmer.

FIG. 4 is a functional block diagram illustrating various components of an external programmer 40 for an implantable stimulator 34. Although the components shown in FIG. 4 are described in reference to external programmer 40, the components may also be included within clinician programmer 20 or patient programmer 22 shown in FIG. 1. As shown in FIG. 4, external programmer 40 includes processor 53, memory 55, telemetry module 67, user interface 59, and power source 61. In general, processor 53 controls user interface 59, stores and retrieves data to and from memory 55, and controls transmission of data with implantable stimulator 34 through telemetry module 67. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 34, such as programs, values of parameters of programs, or other therapy delivery values.

A clinician or patient 36 interacts with user interface 59 in order to, for example, manually select, change, or modify programs, e.g., by adjusting voltage or current amplitude, adjusting pulse rate, adjusting pulse width, or selecting different electrode combinations or configurations, and may provide efficacy feedback or view stimulation data. User interface 59 may include a screen and one or more input hard and/or soft key buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Using the techniques of this disclosure, a clinician or patient 36 may define one or more desired therapy targets (e.g., pain areas) and programs corresponding to the defined therapy target using interface 59. The programs for the different therapy targets may be organized into slots, where a slot corresponds to a therapy target and includes the programs associated with that therapy target. Each slot may have one or more programs defining therapy for the therapy target of the slot, and one program in each slot may be selected and activated based on a selection made by a user or automatic selection based on detected conditions such as, for example, patient posture. Using the user interface 59, a user may define the parameters for each program or each group of programs (i.e., slot) associated with a therapy target. For example, each therapy target may have parameters that are the same for all programs targeting that therapy target, in addition to parameters specific to each of the programs, as will be discussed in more detail below.

Using user interface 59, a user may view an image representation of the patient body showing a paresthesia map. The user may also view an image representation of the patient body showing a pain map. In one example, the user may also view an image representation of the patient body showing a dermatomal map. The paresthesia map may show the areas of the patient at which the patient experiences the sensation of paresthesia when stimulation is delivered according to a program, and thereby illustrate the therapy target, based on a selected therapy program. The paresthesia map changes based on the parameters defined for a program. The pain map may show areas of the patient at which the patient experiences pain, and therapy illustrate the therapy targets that require therapy.

In an example, the paresthesia map and the pain map may be overlaid to determine or illustrate the amount of overlap between the two maps. The amount of overlap may be an indication of the therapy efficacy of a selected program for the associated therapy target. During programming, as the user changes parameters, the paresthesia map may change accordingly, and the user may change the programmed parameters based on the efficacy information and/or overlap between the paresthesia map and pain map. In some examples, for certain therapies, other outcome representations may be used. For example, deep brain stimulation (DBS) for Parkinson's disease may indicate tremor measures for each extremity as shown on a body map.

Telemetry module 67 allows the transfer of data to and from stimulator 34. Telemetry module 67 may communicate automatically with stimulator 34 at a scheduled time or when the telemetry module detects the proximity of the stimulator. Alternatively, telemetry module 67 may communicate with stimulator 34 when signaled by a user through user interface 59. To support RF communication, telemetry module 67 may include appropriate electronic components, such as amplifiers, filters, mixers, encoders, decoders, and the like. In other examples, telemetry module 67 may employ other communication standards such as, for example, Bluetooth® and telemetry module 67 may include the appropriate Bluetooth® components.

Programmer 40 may communicate wirelessly with implantable stimulator 34 using, for example, RF communication or proximal inductive interaction or other communication standards such as, for example, Bluetooth®. This wireless communication is possible through the use of telemetry module 67 which may be coupled to an internal antenna or an external antenna. Telemetry module 67 may be similar to telemetry module 57 of implantable stimulator 34. In accordance with this disclosure, programmer 40 may communicate with stimulator 34, via telemetry module 56 to retrieve information such as, for example, programs defining the therapy being delivered and the different program options for each therapy target, which may be stored in memory 52 for viewing and/or manipulation by a user via user interface 59.

Programmer 40 may also be configured to communicate with another computing device via wireless communication techniques, or direct communication through a wired, e.g., network, connection. Examples of local wireless communication techniques that may be employed to facilitate communication between programmer 40 and another computing device include RF communication based on the 802.11 or Bluetooth specification sets, infrared communication, e.g., based on the IrDA standard. For example, programmer 40 may be a clinician programmer and may be configured to communicate directly with patient programmer 22 (FIG. 1) to store therapy parameter configurations in patient programmer 22 for subsequent transfer to the IMD.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

As noted above, a user may utilize a programmer 40 (e.g., programmer 20 or 22 of FIG. 1) to define stimulation therapy programs for different therapy targets by selecting stimulation therapy program parameters associated with each of the programs. For each therapy target, different stimulation therapy programs may be defined based on different variables. For example, stimulation therapy programs may vary based on posture (e.g., standing, lying down, sitting, or the like), amount of activity (e.g., low or high amount of activity), intensity of symptoms (e.g., amount of tremor, heart rate, or the like), and so forth. In one example, the user may utilize programmer 40 to further organize the therapy programs in different slots according to therapy targets. Additionally, the user may utilize programmer 40 to select a stimulation therapy program within each slot, where the selected programs are applied to the patient by IMD 34. In some examples, a device may automatically perform the organizing of the therapy programs into the different slots and/or the selection of the programs. The device may be a programmer (e.g., clinician or patient programmer) or the IMD. The automated organization and/or selection of the stimulation therapy programs may be based on factors associated with the variables used to define the stimulation therapy programs, e.g., posture, activity, and symptoms. In one example, the automated organization and/or section of the stimulation therapy programs may be based on data specific to the patient, e.g., responsiveness to different therapies, indications by patient as to efficacy of therapy, and the like.

In one example, programmer 40 may transfer the defined stimulation therapy programs to IMD 34 using their respective telemetry modules. Processor 50 of IMD 343 may automatically organize the programs into the slots and options based on certain information, e.g., data specific to the patient, data specific to the condition, and/or information sent with the programs. Some or all of the information that processor 50 utilizes to automatically organize the stimulation therapy programs may be stored in memory 52. In another example, programmer 40 may organize, automatically or through user input, the stimulation therapy programs according to the different information, and transfer the organized programs to IMD 34. In one example, where IMD 34 organizes the programs into the different slots, the organized programs may be transferred to programmer 40.

The organized programs, e.g., the slots corresponding to the different therapy targets, may be then used to select a stimulation therapy program from each slot as necessary. In one example, selection of programs for a given slot may be automated, where a processor (e.g., processor 50 of IMD 34 or processor 53 of programmer 40) may select the active program in each slot automatically. As noted above, the automated selection may be based on one or more variables, e.g., posture (e.g., standing, lying down, sitting, or the like), amount of activity (e.g., low or high amount of activity), intensity of symptoms (e.g., amount of tremor, heart rate, or the like), and so forth. In one example, IMD 34 may be capable of detecting the posture of a patient and utilize the detected posture to select a program from a slot with programs associated with different postures.

In one example, IMD 34 may be capable of sensing and monitoring different parameters, e.g., brain signals, sleep states, extent of tremors, and so forth, and utilize the sensed parameter to select an appropriate program. For example, in a system that deliver deep brain stimulation (DBS) therapy, programs in one slot may provide stimulation to reduce tremor in a corresponding portion of the patient's body (e.g., on a particular side or in a particular limb). One or more sensors (e.g., accelerometer) associated with IMD 34 may be utilized to monitor the amount of tremor in the patient. IMD 34 may determine based on data from the one or more sensors the amount of change in tremor, and when the change is significant, IMD 34 may automatically trigger a change in the selected program in a given slot.

As another example, bioelectrical signals may be monitored and sensed with a patient's brain. Such signals may include, but are not limited to, an electroencephalogram (EEG) signal, an electrocorticogram (ECoG) signal, a local field potential (LFP) sensed from within one or more regions of brain 16, and/or action potentials from single cells within brain 16. IMD 34 may utilize these sensed signals to select a different program for one or more slots. Selection of a program in one or more slots may occur, for example, at the detection of the onset of a seizure. Other types of signals and patient states may be monitored to control an automated selection of a program for a given slot.

Figure 5:
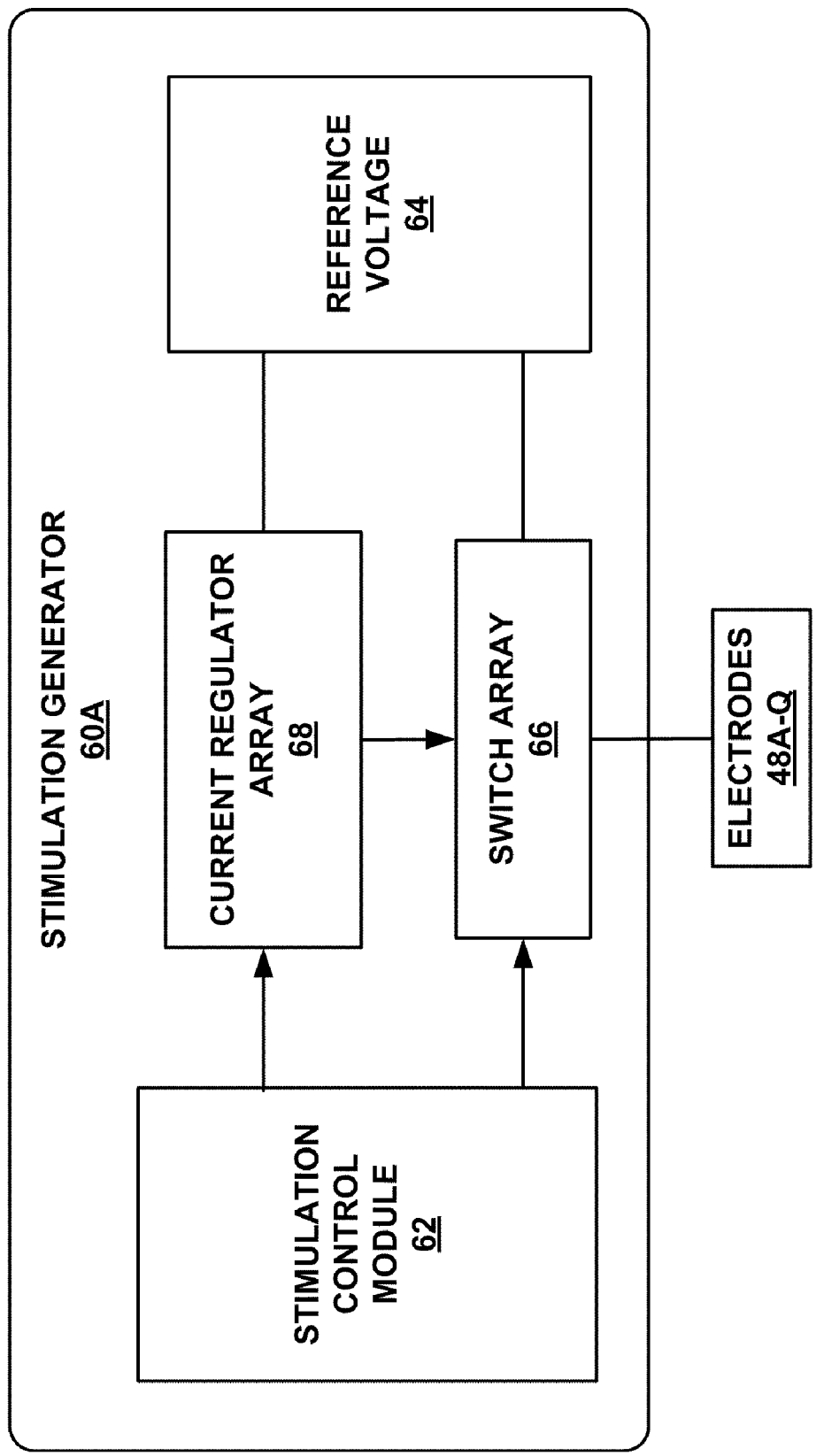
FIG. 5 is a block diagram illustrating various components of an example electrical stimulation generator for use in the implantable electrical stimulator of FIG. 3.

FIG. 5 is a block diagram illustrating various components of an example stimulation generator 60A. Stimulation generator 60A may be used with an implantable stimulator, e.g., to perform the functions of stimulation generator 60 as described with reference to FIGS. 1-3. Although described with respect to implantable stimulator 34, stimulation generator 60A may also be used for implantable stimulator 4, or other types of stimulators. In the example of FIG. 5, stimulation generator 60A is selectively, e.g., based on a signal from processor 50 (FIG. 3), configured to deliver constant current stimulation pulses to patient 36 via various electrode combinations. However, the disclosure is not limited to examples in which regulated current pulses are delivered. In other examples, stimulation generator 60A may provide continuous, regulated current waveforms, rather than regulated current pulses. In still other examples, stimulation generator 60A may deliver combinations of continuous waveforms and pulses, or selectively deliver either continuous waveforms or pulses. Stimulation generator 60A may generate either constant current-based or constant voltage-based stimulation in the form of pulses or continuous waveforms. In yet other examples, stimulation generator 60A may use a voltage regulator instead of a current regulator.

In the example illustrated in FIG. 5, stimulation generator 60A includes stimulation control module 62, reference voltage source 64, switch array 66, and current regulator array 68. Reference voltage source 64 may provide operating power to current regulator array 68, and may include a regulated voltage that sets the level of the reference voltage. As shown in FIG. 5, reference voltage source 64 may be coupled to provide operating power for the current regulator array 68 and provide a reference voltage for connection to electrodes 48A-48Q for an unregulated mode of electrode operation. In other examples, however, the voltage level of the reference voltage and the operating voltage level provided to regulated current source array 68 may be different.

Stimulation control module 62 forms a stimulation controller that controls switch array 66 and current regulator array 68 to deliver stimulation via electrodes 48A-48Q. Stimulation control module 62 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 62 may control delivery of electrical stimulation according to one or more programs that may specify stimulation parameters such as electrode combination, electrode polarity, stimulation current amplitude, pulse rate, and/or pulse width as well as the percentage of source current distributed among or contributed by a housing anode and one or more lead anodes on one or more leads, and the percentage of sink current sunk by one or more cathodes. Programs may be defined by a user via an external controller and downloaded to an implantable stimulator 4 or 34 for use by stimulation control module 62.

Current regulator array 68 includes a plurality of regulated current sources or sinks Again, a current regulator may function as either a current source or sink, or be selectively configured to operate as either a source or a sink. For convenience, however, the term "current regulator" may be used in some instances to refer to either a source or sink. Hence, each of the current regulators in current regulator array 68 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements.

Each switch of switch array 66 couples a corresponding one of electrodes 48 to either a corresponding bidirectional current regulator of current regulator array 68 or to reference voltage 64. In some examples, stimulation control module 62 selectively opens and closes switches in switch array 66 to configure a housing electrode, e.g., electrode 48Q, and one or more of electrodes 48A-48P on one or more leads as regulated electrodes by connection to regulated current sources or sinks in current regulator array 68. In other examples, stimulation control module 62 may selectively open and close switches in switch array 66 to configure either the housing electrode, e.g., electrode 48Q, or an electrode on the lead as an unregulated electrode by connection to reference voltage 64. In addition, stimulation control module 62 may selectively control individual regulated current sources or sinks in current regulator array 68 to deliver stimulation current pulses to the selected electrodes.

Reference voltage 64 may be a high or low voltage supplied by a regulated power source, depending on whether an electrode is programmed to be an unregulated source (high voltage rail) or unregulated sink (low voltage rail). Hence, reference voltage 64 may produce high and low reference voltages for selective coupling to unregulated, reference electrodes as needed given the selected electrode configuration. A regulated power source may produce one or more regulated voltage levels for use as reference voltage 64 and for use as a power rail for current regulator array 68. Again, although the same reference voltage 64 is coupled to current regulator array 68 in FIG. 5, different voltage levels could be used for the reference voltage coupled to switch array 66 and the operating voltage level provided to the regulated current source array. A regulated power source may generate the regulated voltages from voltages provided by a power source 54 (FIG. 3), such as a battery.

Stimulation control module 62 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with reference voltage 64. As previously described, in some examples, two or more regulated stimulation electrodes 48 may be intentionally programmed to deliver different amounts of current such that the regulated electrodes produce an unbalanced current distribution.

To provide individual control of electrodes 48 as either regulated electrodes or as unregulated, reference electrodes, stimulation control module 62 controls operation of switch array 66, and current regulator array 68. When stimulation is delivered to patient 36, for the example of current pulses, stimulation control module 62 controls switch array 66 to couple selected stimulation electrodes for a desired electrode combination to respective current regulators of current regulator array 68 or to reference voltage 64, as needed. Stimulation control module 62 controls the regulated bidirectional current sources of current regulator array 68 coupled to regulated electrodes to source or sink specified amounts of current. For example, stimulation control module 62 may control selected current sources or sinks to on a pulse-by-pulse basis to deliver current pulses to corresponding electrodes.

Stimulation control module 62 also deactivates the regulated bidirectional current regulators of current regulator array 68 tied to inactive electrodes, i.e., electrodes that are not active as regulated electrodes in a given electrode configuration. Each regulated bidirectional current regulator of current regulator array 68 may include an internal enable switch controlled by stimulation control module 62 that disconnects regulated power source 64 from the current regulator or otherwise disables the current source when the corresponding electrode is not used as a regulated electrode to deliver stimulation.

Figure 6A:
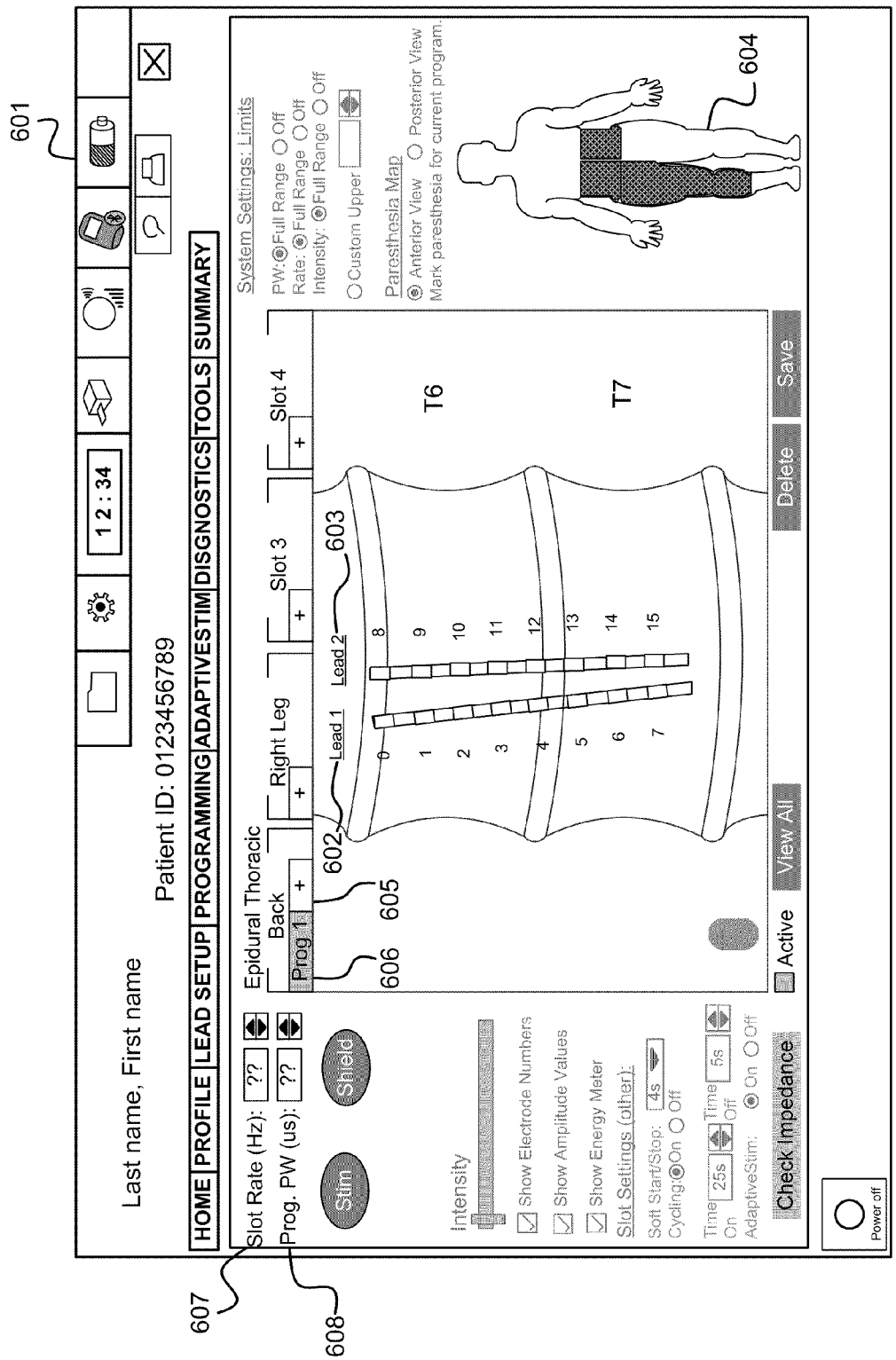
FIGS. 6A-6N illustrate an example sequence of programmer screen shots, in accordance with this disclosure.

FIGS. 6A-6N illustrate an example sequence of programmer screen shots, in accordance with this disclosure. A programmer, e.g., programmer 40 (FIG. 2), may receive user input via the user interface 59 to set up leads for use in defining stimulation programs. A stimulation program may be a program defined to deliver therapy to a therapy target, and may be delivered by an implantable stimulator, individually or in combination with other programs, e.g., on a time-interleaved basis. A program may define an electrode combination, including a selected set of electrodes for delivery of stimulation and polarities of such electrodes, pulse current, or pulse voltage amplitudes delivered by respective electrodes, pulse width and pulse rate. A user may set up a profile for a patient and proceed to configure placement of the leads, using the user interface 59.

FIG. 6A illustrates a screen shot of a programmer screen 601 of user interface 59 of programmer 40 after the user has completed lead setup, e.g., upon specifying lead type, lead configuration, lead positions, and/or other lead characteristics. Following lead setup, the programmer screen 601 may show the placement of the electrodes carried by the leads as shown with a graphical representation of the leads 602 and 603 over an anatomical image of the implantation region. In some examples, the image of the implant region may be an actual anatomical image obtained by fluoroscopy or other imaging methods. In other examples, the image of the implant region may be a graphical representation of a therapy region. One or more examples of acquiring and storing a fluoroscopic image of a therapy region in a patient may be described in U.S. patent application Ser. No. 12/771,652, entitled "STORING IMAGE OF THERAPY REGION IN IMPLANTABLE MEDICAL DEVICE," filed Apr. 30, 2010, the entire content of which is incorporated herein by reference.

The programmer may allow the user to program several slots, for example, slots 1-4 as shown in FIG. 6A. The user may use one or more of the slots to define programs associated with therapy targets, where each slot is populated with programs that define therapy for the therapy target associated with the slot, from which a user may select a program to activate, and the selection of a program in one slot is independent of other slots. For example, a user may create 4 slots corresponding to 4 therapy targets, and define one or more programs for each slot, where the programs correspond to therapies associated with the therapy target of the slot. A user may select to activate a program in each slot, where the selection of a program may be done by the user, the patient, or automatically. At a later time, the user may select to activate a different program for one of the slots, which may replace the active program in that slot, without affecting the active programs in other slots. In one example, the active program may be selected automatically based on a sensed parameter associated with the patient, where a program associated with the sensed parameter may be activated. The parameter may be, for example, a posture of the patient, an activity level, a time of day, or the like. In another example, a user may select to activate one program for each slot by selecting a specific program in each slot regardless of selected programs in other slots. In another example, a user may activate programs simultaneously in all slots by utilizing a mode where corresponding programs from each of the slot may be selected in one action, for example, a user may select the first program in each slot, or the second program in each slot, or the third program in each slot, and so forth.

In the example of FIG. 6A, the user has only used two of the slots by defining them according to the therapy target for the particular patient, e.g., back and right leg. A combined pain and paresthesia map 604 may be provided to highlight the therapy targets in the patient and the paresthesia coverage provided by the selected programs to show the efficacy of the active program relative to the therapy target. In one example, the therapy target, e.g., pain area, may be represented using one color, shade, or pattern, and the paresthesia area may be represented using a second color, shade, or pattern to show the area affected by the therapy of the active program. Each therapy target may correspond to one or more of the defined slots, i.e., the program selected for a given slot may target pain in a particular area. For example, slot 1 may contain a stimulation program selected to alleviate pain/symptoms in the area associated with slot 1, i.e., a program selected to alleviate pain in the back of the patient. A first color, texture, symbol or other indicator may be used to highlight particular areas of pain, such as back, right leg, left leg, or the like. A second color, texture, symbol or other indicator may be used to highlight paresthesia coverage of such therapy targets upon application of stimulation therapy according to the programs selected for the slots.

The user may define programs within each slot by defining parameters associated with a program and adding it to the list of programs for each slot. In one example, the number of programs that can be defined per slot may be predetermined in advance or limited based on the overall number of programs defined for all slots. The number of programs in a slot may depend on the different therapy options for the slot, and the therapy options may be based on different parameters for each of the programs in the slot. For example, each programs may be defined with one or more different parameters, e.g., electrode configuration, amplitude, pulse width, etc. The different therapy options, or programs, may be placed in slots based on the therapy target associated with the therapy options, and may be selected for programming the IMD for therapy delivery. Following the lead setup, the user may start defining programs for the different slots associated with the patient based on the therapy targets for that patient. The user may click the add button 605 under one of the slots, for example, the back slot, to add to the list of programs or therapy options for that slot. As a result, a button 606 for the first program may be activated and highlighted to indicate which program and slot the user is programming. Prior to defining the slot rate 607 and program pulse width (PW) 608, other options may not be made available to the user to manipulate and, as a result, may remain grayed out until the user enters values for the slot rate 607 and the program pulse width 608. Upon selecting the slot rate and program PW, various additional controls may become available for manipulation in programmer screen 601.

Figure 6B:
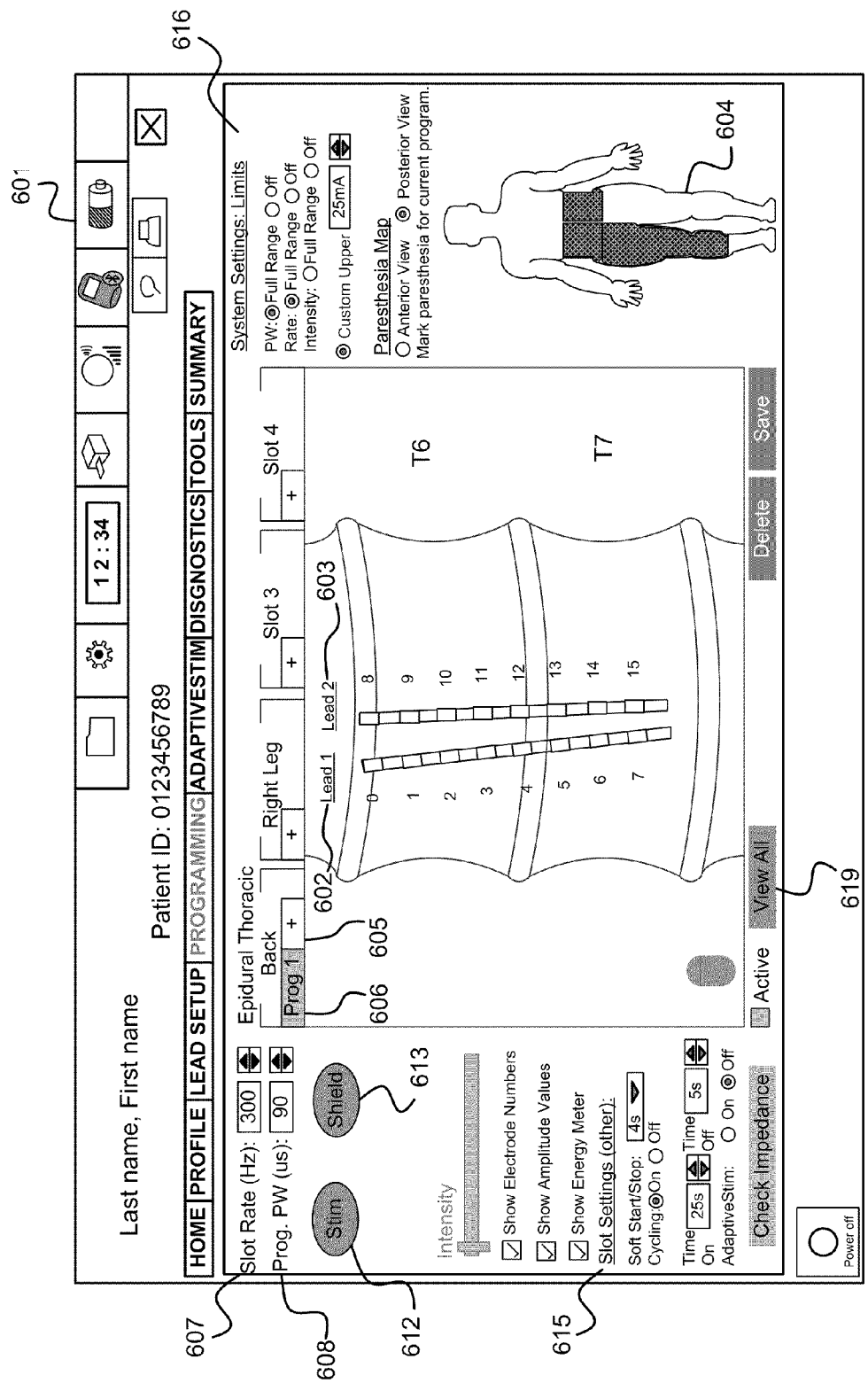

FIG. 6B illustrates a screen shot of the programmer screen 601 when the user starts programming a therapy program. The user may define the slot rate 607 and the program pulse width 608. The slot rate 607 may indicate the frequency (e.g., pulse rate) of the signal associated with the stimulation applied to the therapy target defined by the active slot for which the user is creating the current program. In this example, the user is programming a therapy program under the slot for the back as the therapy target, for which the rate defined by the user is 300 Hz. The slot rate may be a global parameter such that it applies to all the programs in the particular slot with which it is associated, therefore, different slots may have different slot rates and PWs, and adjustments to slot rate and PW may be applicable to the selected slot during programming. The program pulse width 608 may indicate the width of the pulse associated with the program being currently programmed by the user, in this example, program 1 in the back slot may have a pulse width of 90 micro seconds. The user may enter a value for each of the slot rate 607 and the program pulse width 608, and use the up and down arrows to increase or decrease the values. In an example, the values for each of the slot rate and the program pulse width may be limited to minimum and maximum values below and above which, respectively, a user may not specify a value. When the user specifies a value for the slot rate 607 and the program pulse width 608, other options may become selectable. For example, the STIM button 612 and SHIELD button 613 may become highlighted and may be selected by the user to indicate a program-specific stimulation (cathodic) region and/or shield (anodic) region, respectively, to be delivered via electrodes on one or more leads.

Additional options may also become highlighted and available for a user to select as shown in the lower left corner of the screen 601. For example, the user may select to show the electrode numbers (e.g., 0 through 15 for sixteen electrodes in a 2×8 lead configuration), show pulse amplitude values for pulses delivered via particular electrodes (e.g., current values in milliamps (mA)), and show the energy meter associated with the leads (e.g., in terms of the time before recharge of the battery used to supply the power for stimulation is required given the selected parameter settings). In the example of FIG. 6B, while the boxes corresponding to these options are checked, the values associated with the options may not appear until the user selects STIM button 612 to program the stimulation zone.

Other settings 615 associated with the current slot may also be available for the user to define and manipulate such as, for example, the soft start/stop time (the amount of time it takes stimulation to go from 0 to its full amplitude), whether cycling is on or off (whether the cycling feature is on or off, if cycling is on, then the cycling on/off times are applied to the stimulation as a duty cycle, and if cycling is off, then stimulation is always on), the ON and OFF times (how long stimulation is on and how long it is off for programs in a specific slot), and whether the adaptive STIM is on or off (determines whether PRS is on for a particular slot). In this example, the soft start/stop time may be selected from a drop-down menu, but may be also defined by the user with maximum and minimum limitations above or below which their values may not go. Similarly, with the ON and OFF times may be defined by the user, and may also have maximum and minimum values, which may not be exceeded. In one example, the ON and OFF cycling times may be grayed out and made unavailable if the user selects cycling to be OFF.

Other options may also be highlighted and available for a user to select as shown in the upper right corner of the screen 601. Settings 616 associated with the system may also be available for the user to select such as, for example, whether the pulse width is full range or off, whether the rate is full range or off, and whether the intensity is full range or off Selecting "full range" for a parameter allows the patient to have full freedom to adjust the parameter between a maximum and minimum value, while selecting "off" prevents a patient from making adjustments. In one example, the patient may have the freedom to make adjustments, and the patient may utilize a patient programmer to make such adjustments.

In some examples, a specific limit value may also be configurable, allowing a patient to adjust a parameter within the specified bounds. In an example, the user may define an upper intensity or amplitude value. In the example of FIG. 6B, the upper amplitude values is set to 25 mA.

The user may also be able to change the view of the pain/paresthesia map 604 to either an anterior or posterior view, or view both anterior and posterior views simultaneously. In another example, the paresthesia map may be 3-dimensional and may have more views that a user may select. In some examples, map 604 may be a dermatomal map. In one example, the IMD may have sensing capabilities, allowing it to sense activity in an anatomical region. In one example, the sensing capabilities of the IMD may be combined with feedback from the patient to generate the paresthesia and/or dermatomal maps of the patient. In this example, therapy configuration may include additional configurations for slot parameters related to sensing waveforms and physiological activities. The additional parameters may include parameters such as gain, filter characteristics, sampling rate, thresholds for event detection, and actions to execute when certain events or physiological activities are detected.

Figure 6C:
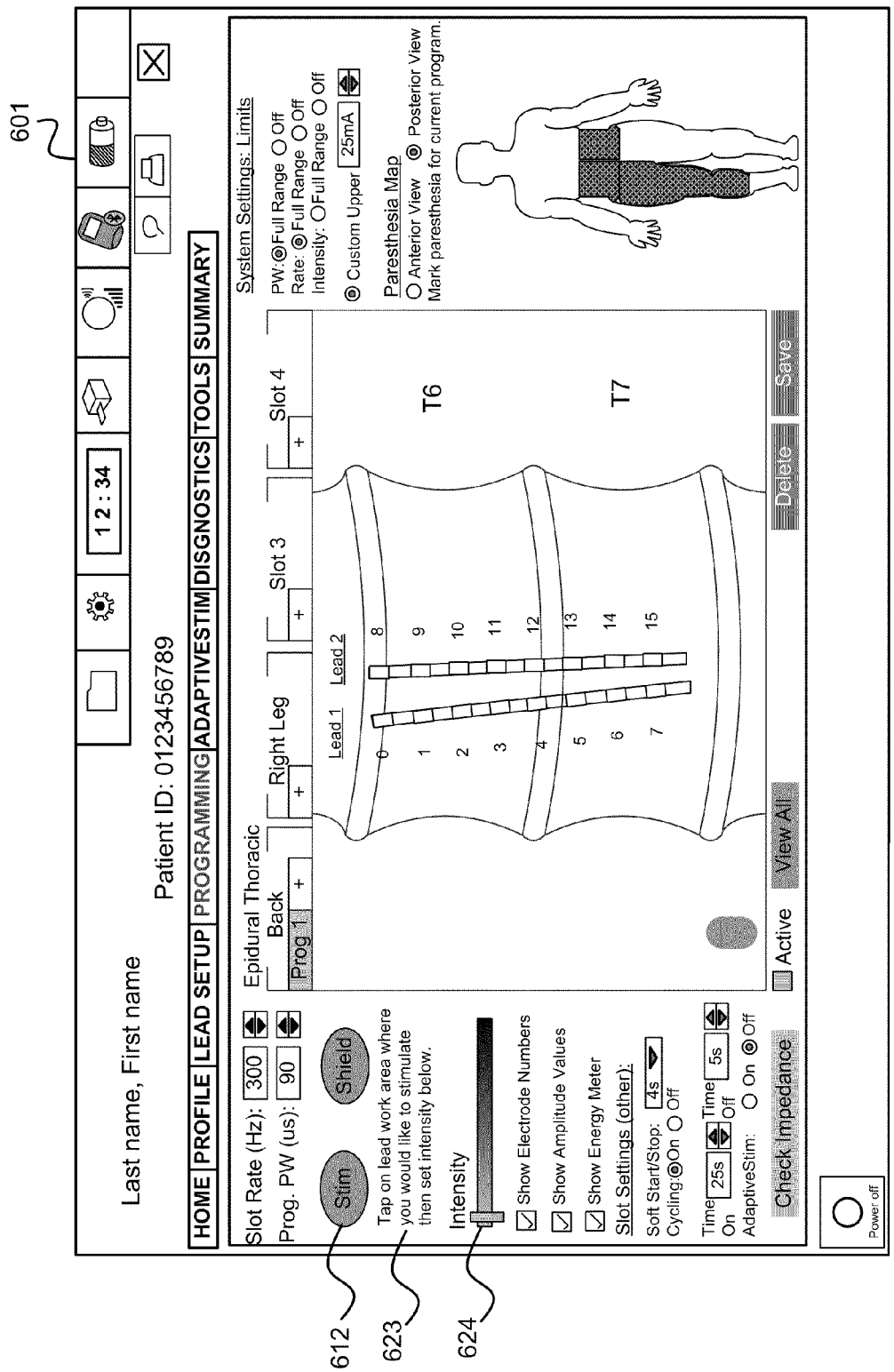

FIG. 6C illustrates a screen shot of the programmer screen 601 when the user selects the STIM button 612. While setting up a program (e.g., program 1) within a slot (e.g., back slot), the user may utilize the STIM function to define the region where stimulation therapy may be applied by the electrodes. When the user selects the STIM button 612, the user interface may display a message 623 indicating to the user to tap on the lead work area where the user may want the stimulation to be applied. Selecting the STIM button 612 may also activate the STIM intensity scale 624, which allows the user to select the intensity of the stimulation field defined by the user.

Figure 6D:
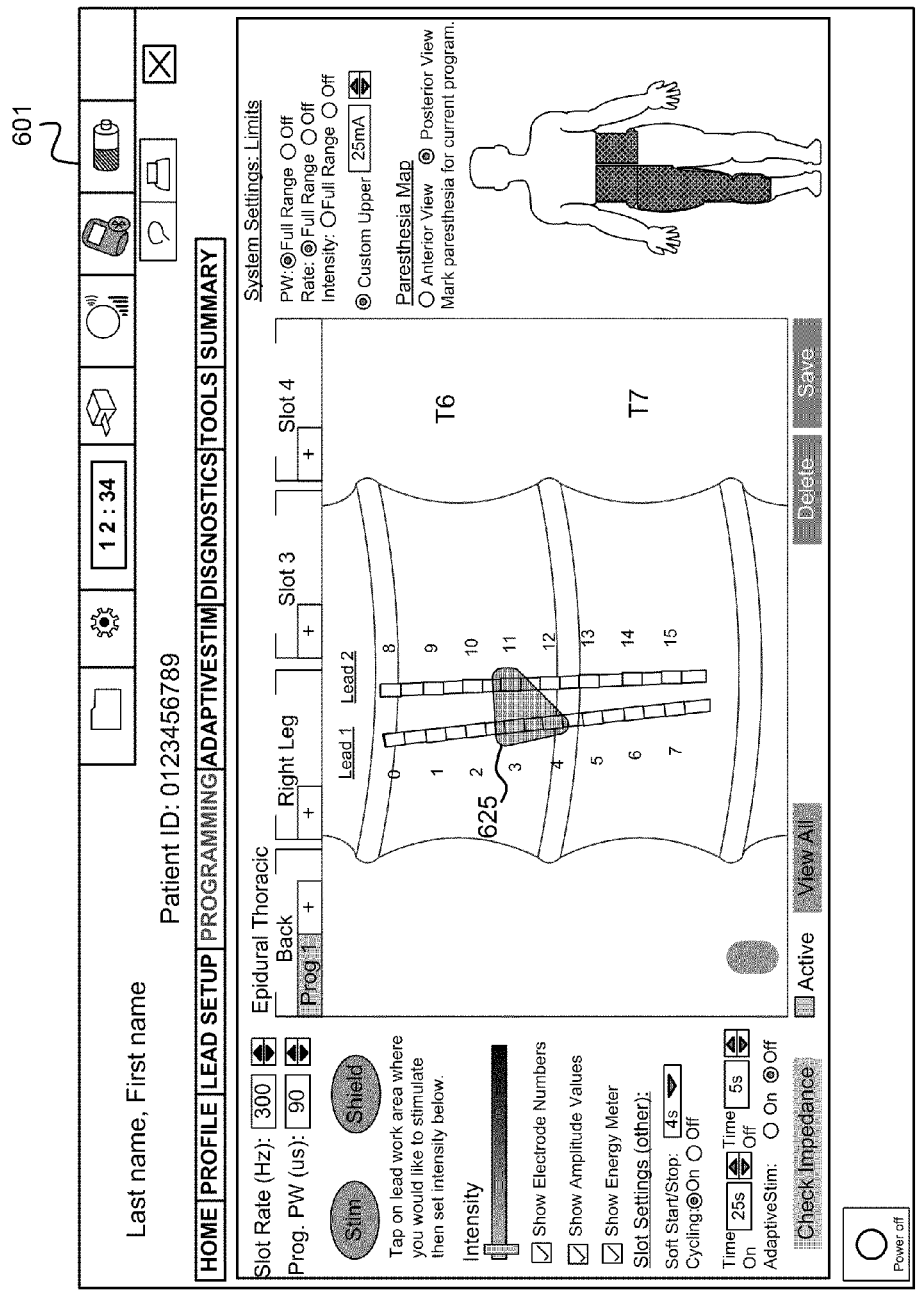
Figure 6E:
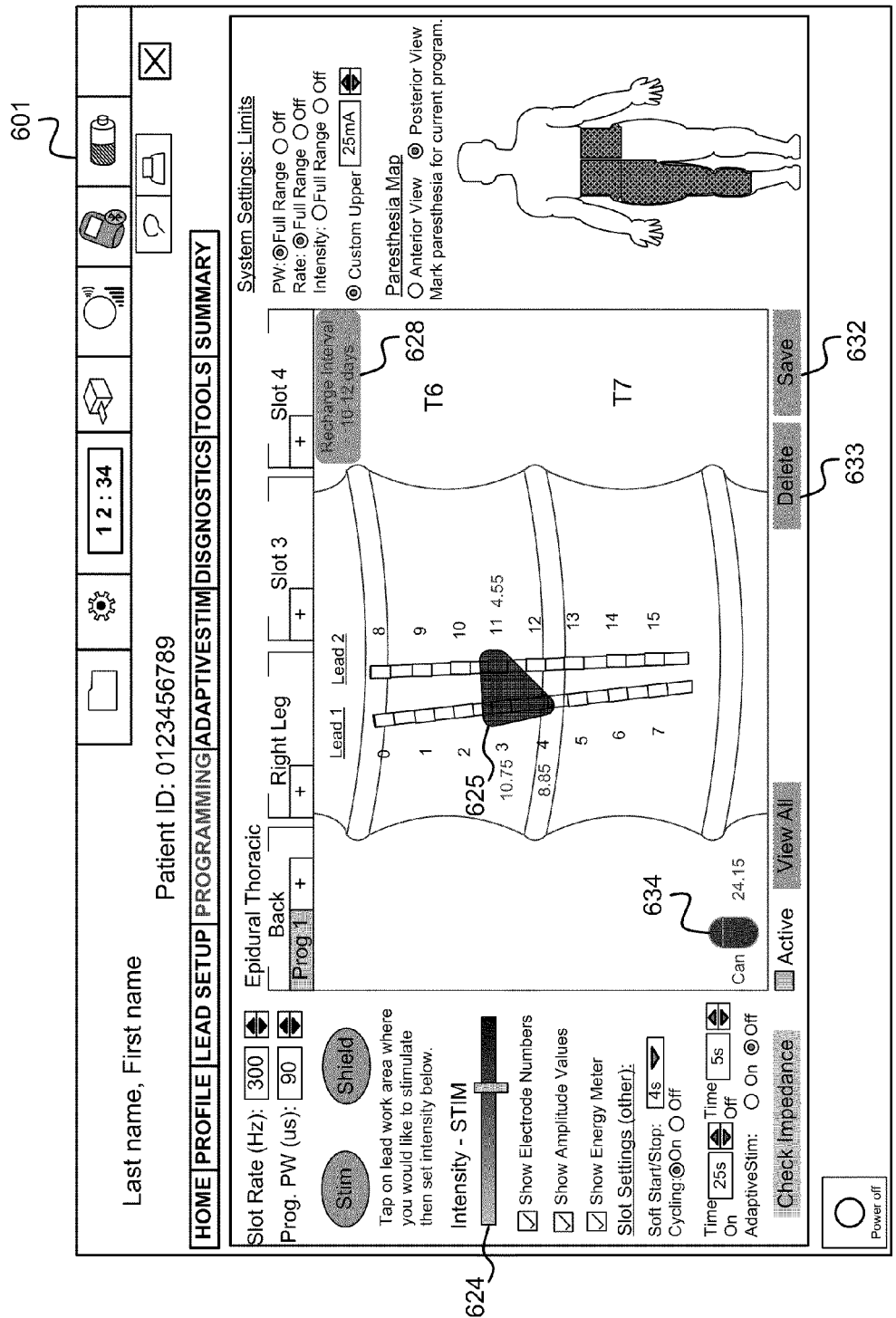

FIG. 6D illustrates a screen shot of the programmer screen 601, where the user may tap on a lead work area where to apply stimulation, and the stimulation field 625 may be displayed showing the electrodes selected as cathodes in response to the selected stimulation field. FIG. 6E illustrates a screen shot of the programmer screen 601, where the user may further manipulate the stimulation field 625. The user may increase the intensity of the stimulation field 625 using the STIM intensity scale 624. As the user increases the intensity of the stimulation field 625, the intensity of the electrodes associated with the stimulation field appears and also begins to increase, indicating the increase in intensity. As the user increases the intensity of the STIM field, and the cathodic current supplied by the corresponding electrodes increases accordingly, the anodic current of the can (i.e., stimulator housing) is automatically adjusted to offset the current delivered by the electrodes on the lead. In this example, an anode on the can sources the current (24.15 mA) that is sunk by the cathodes on the leads (10.75+8.85+4.55), as illustrated by the "can" icon 634 in the lower left corner of the lead work area.

In one example, as the intensity of the stimulation field is increased, the user interface may display an energy meter 628 to indicate a measure of the battery life in terms of a recharge interval. In one example, the energy meter 628 may display the amount of time left until the battery may need to be recharged and/or replaced, e.g., 5-8 hours, 10-12 days. The recharge interval may vary according to the stimulation parameters selected by the user for the program assigned to the slot. In one example, once the user has defined a stimulation field 625 and changed the associated intensity, the user may be given the option to save the current settings as program 1 of this current slot or delete the selected settings, i.e., the stimulation field and intensity, using the save button 632 or delete button 633, respectively.

Figure 6F:
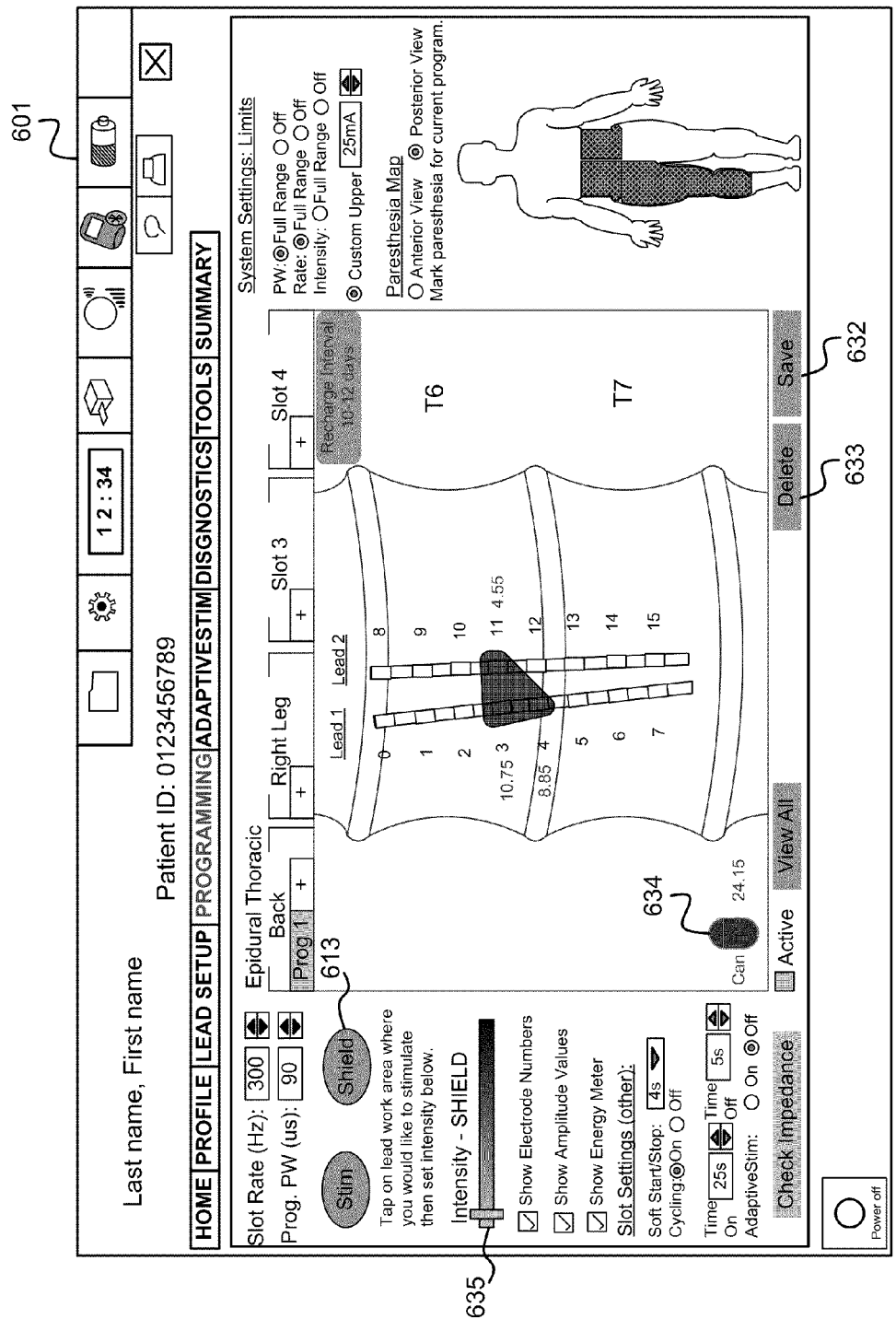

FIG. 6F illustrates a screen shot of the programmer screen 601, where the user may select to add a shield by selecting the SHIELD button 613. The SHIELD may allow the user to define a region to protect from the effects of the STIM field, i.e., to act as a boundary for the region affected by the stimulated therapy, thereby more effectively localizing the stimulation current to a desired therapy target. Once the user selects the SHIELD button 613, the shield intensity control 635 becomes available for the user to select the shield intensity level.

Figure 6G:
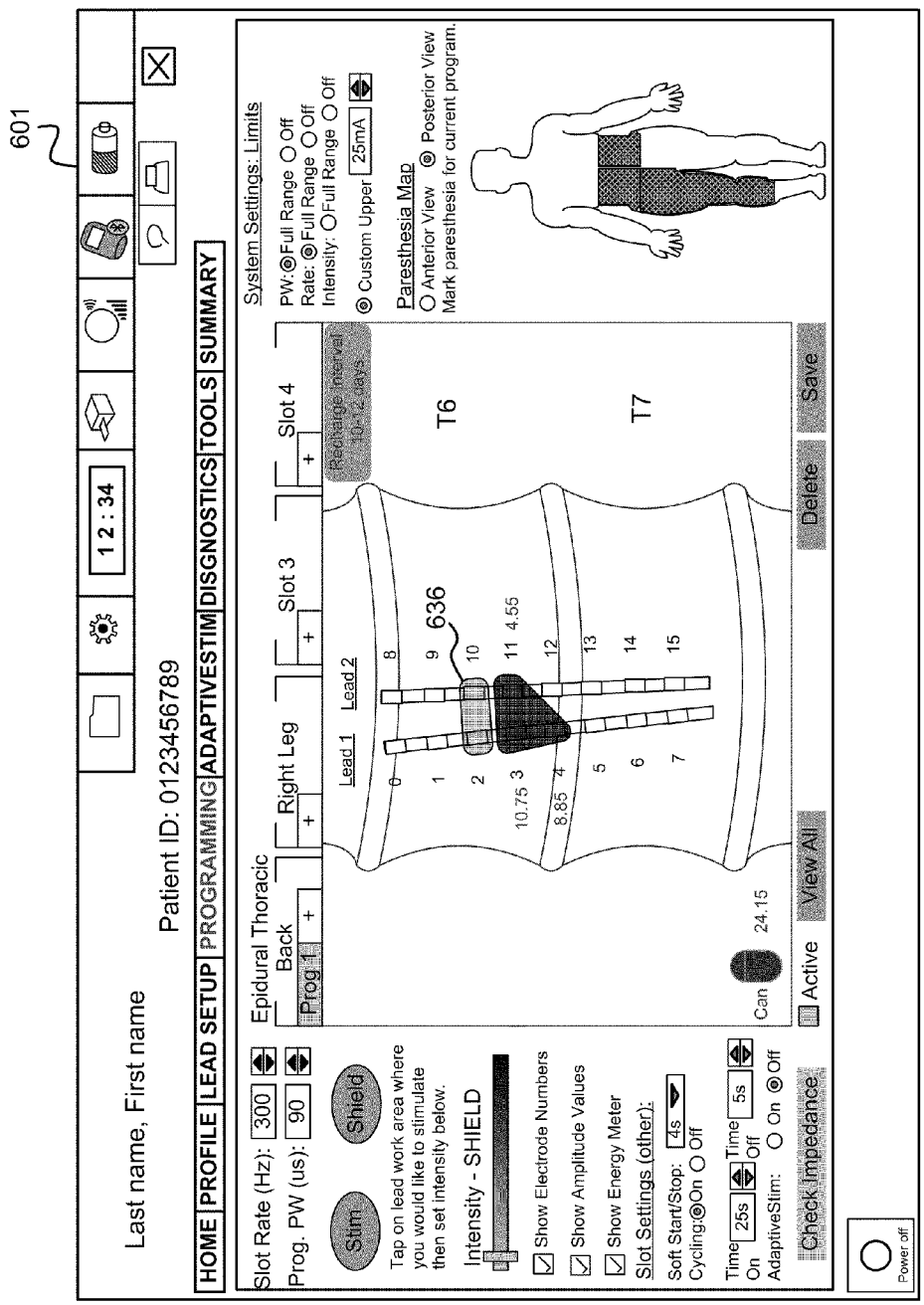
Figure 6H:
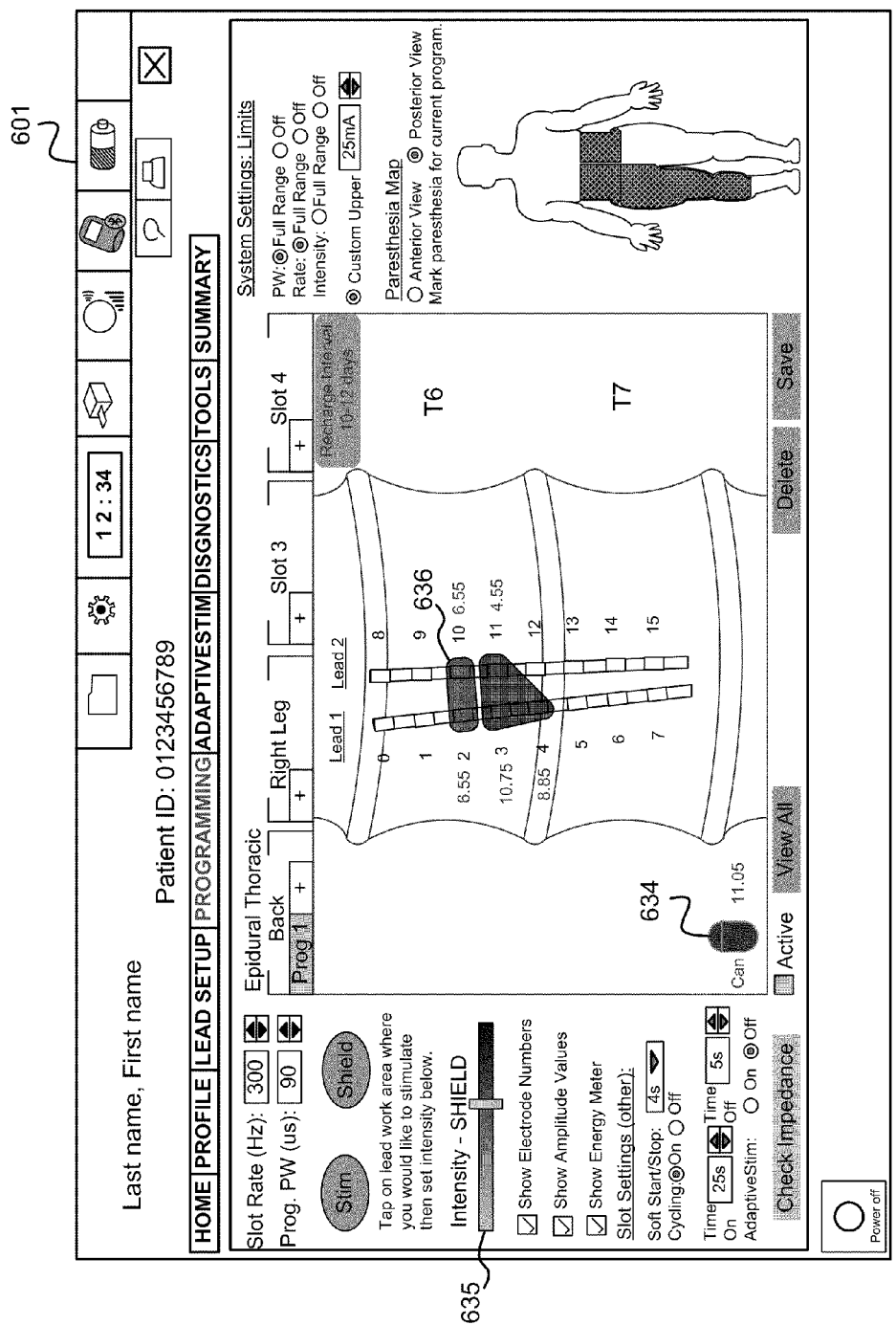

FIG. 6G illustrates a screen shot of the programmer screen 601, where the user may tap on a lead work area to indicate where to apply the shield, and the shield field 636 may be displayed. The shield field 636 may be provided by one or more lead electrodes operating as anodes. In the example of FIG. 6G, electrodes 2 and 10 operate as anodes. FIG. 6H illustrates a screen shot of the programmer screen 601, where the user may further manipulate the shield 636. The user may increase the intensity of the shield 636 using the SHIELD intensity control 635. As the user increases the intensity of the shield 636, the intensity of the electrodes associated with the shield appear and also begin to increase, indicating the increase in intensity. Additionally, as the intensity of the shield 636 is increased, the electrodes that supply the SHIELD provide anodic currents which offset some of the cathodic current provided by the STIM field electrodes. As a result, the anodic current supplied by the can may be affected, and may, as in this example, decrease. In particular, part of the anodic current is delivered by the can while another part of the anodic current is delivered by electrodes 2 and 10. In this example, the sum of these anodic currents at electrode 2, electrode 10, and the can substantially equals the sum of the cathodic currents at electrodes 3, 4, and 11. In this example, stimulation using an omnipolar electrode configuration is described, but other electrode configurations may be contemplated, e.g., bipolar, unipolar, multi-polar. For example, in a bipolar configuration the anode may be on a lead that sources current and the cathode may be on the same or another lead that sinks current.

Figure 6I:

FIG. 6I illustrates a screen shot of the programmer screen 601, where the user may use the pain/paresthesia map 604 to indicate the therapy target for which the current program, i.e., program 1 under the back slot, may be applied. The user may also indicate the paresthesia area on the map 604, which may be used along with the indicated therapy target to determine the efficacy of the therapy program. In one example, a user may have an option to indicate the pain relief of a therapy program in a quantitative manner, e.g., percentage of pain relief, or a scale of pain relief from 1-10, or the like.

The pain/paresthesia map displayed for a program may be the therapy target associated with the slot. The map may also show the paresthesia area for the associated program or programs of the slot, where the parameters defined for the program affect the area affected by the therapy. The pain map and the paresthesia map may be displayed together, where each may be represented by a different color, shade, or pattern, to show the amount of overlap between the two maps. The amount of overlap may be utilized to calculate a therapy efficacy number, which may be a quantification of the effectiveness of the programmed therapy associated with the paresthesia map. The efficacy information may be also displayed for each of the therapy programs, and may be displayed to the user during programming to allow the user to modify the programmed parameters to achieve good efficacy. In the example of FIG. 6I, the lighter gray areas of the paresthesia map may indicate the areas corresponding to the active stimulation program.

Figure 6J:
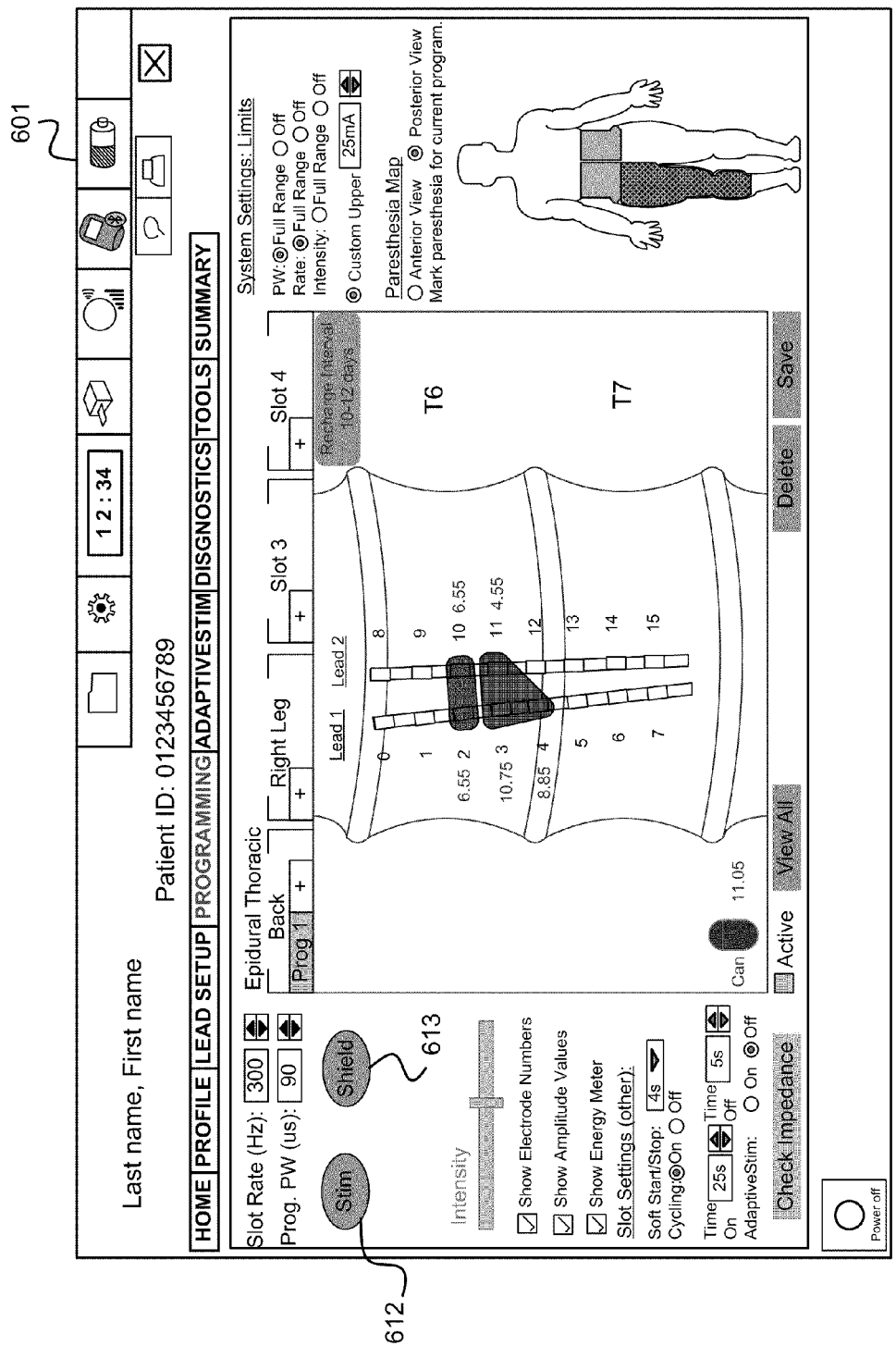

FIG. 6J illustrates a screen shot of the programmer screen 601, where the user may selectively add additional SHIELD and/or STIM zones by clicking the SHIELD button 613 and/or the STIM button 612, respectively. In the examples discussed above, the user may select whether to apply STIM and/or SHIELD by selecting the corresponding button then selecting the electrodes which the user may wish to provide the STIM and/or the SHIELD, and adjust the intensity using the intensity control slider. In another example, the user may be able to select electrodes that the user wishes to program as STIM or SHIELD electrodes by directly selecting the electrodes by clicking or tapping on an electrode or electrodes. The user may then re-click or re-tap on an electrode or group of electrodes to toggle between STIM and SHIELD. The user may then use an intensity control slider or button to change the amount of STIM or SHIELD contributed by each electrode or group of electrode. In one example, the intensity may be expressed in percentages to indicate the percent contribution of each electrode or group of electrodes. In another example, the intensity may be expressed as an absolute value (e.g., in mA or V) to indicate the contribution of each electrode or group of electrodes, as FIG. 6J illustrates.

Figure 6K:
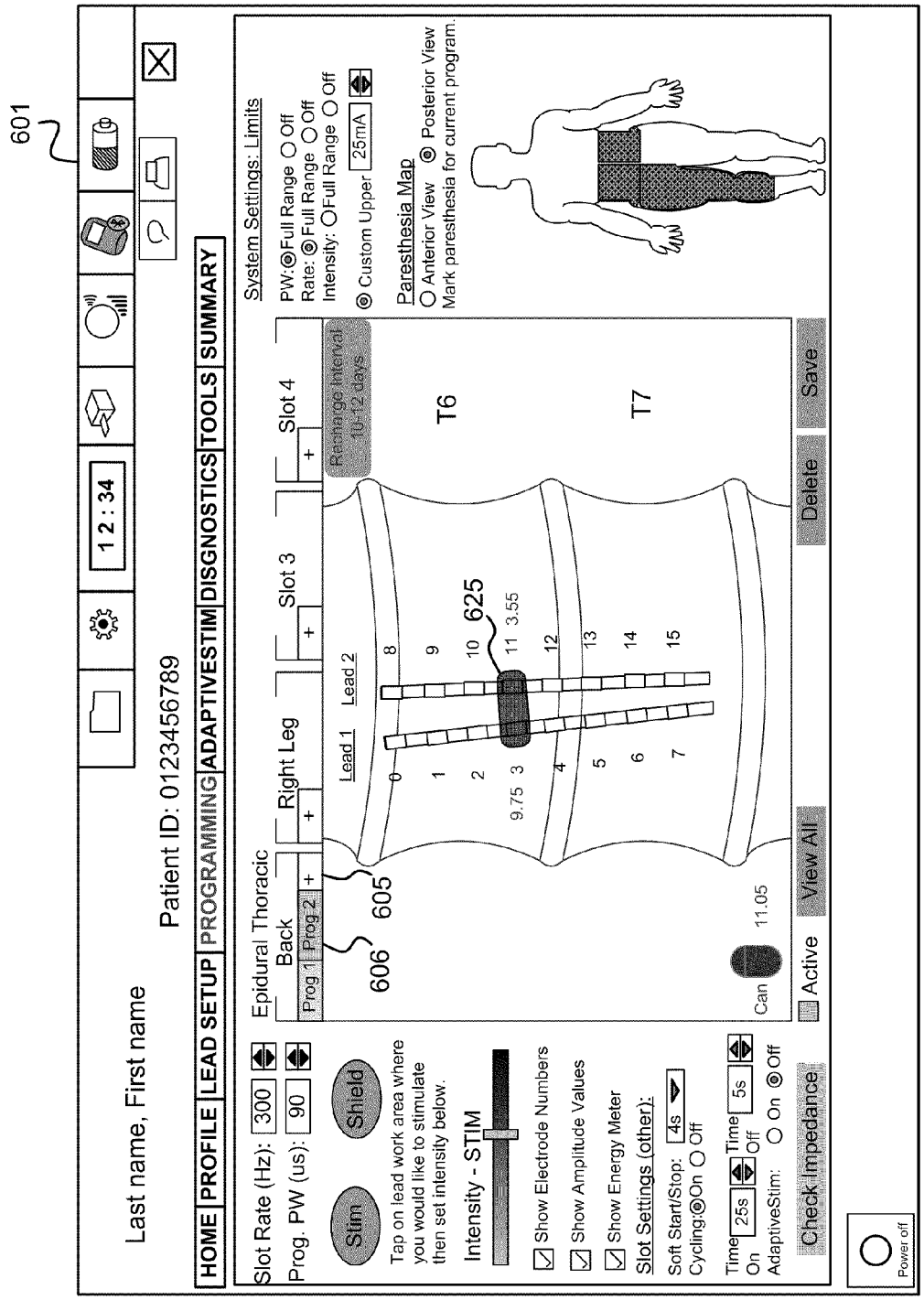
Figure 6L:
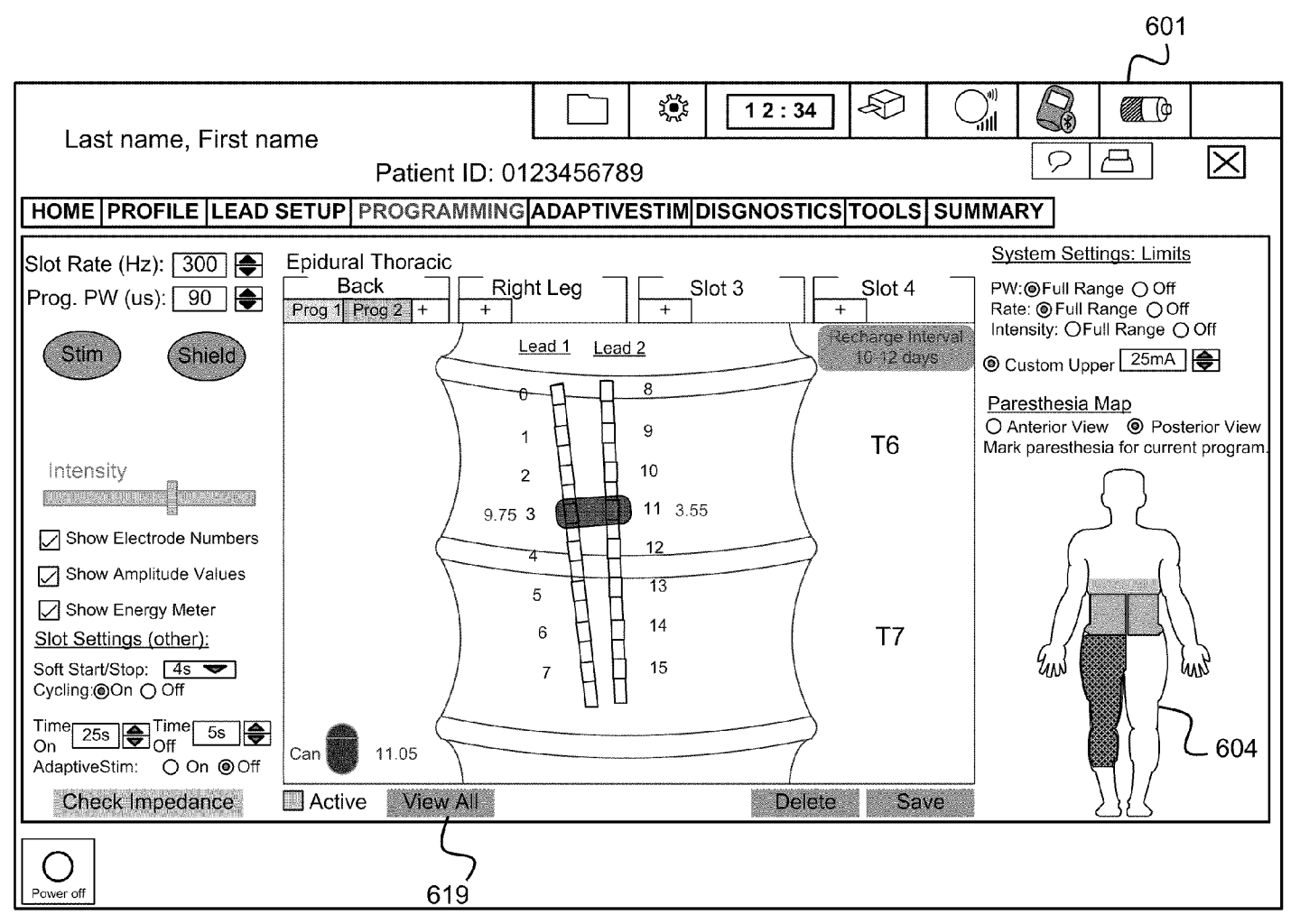
Figure 6M:
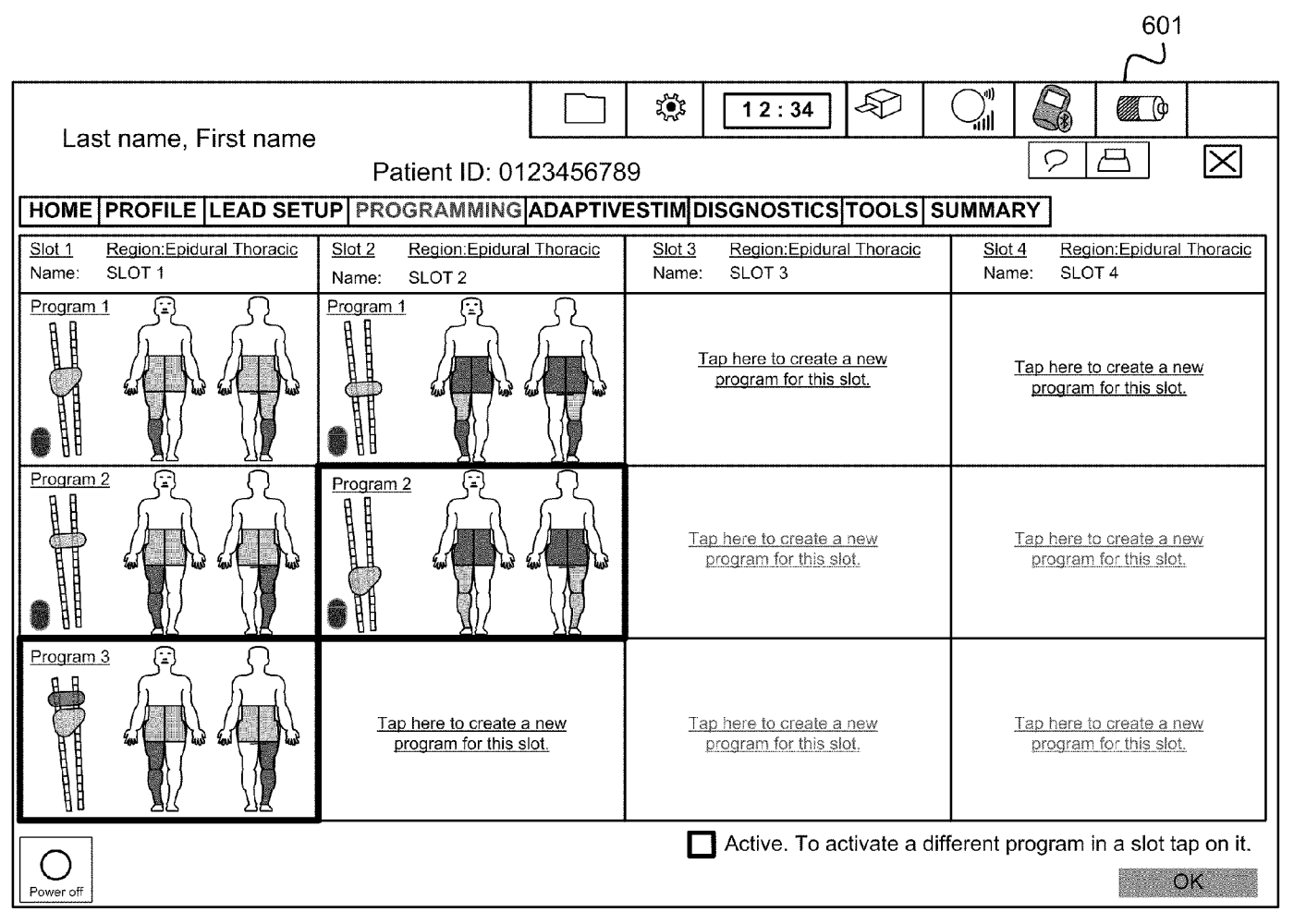
Figure 6N:
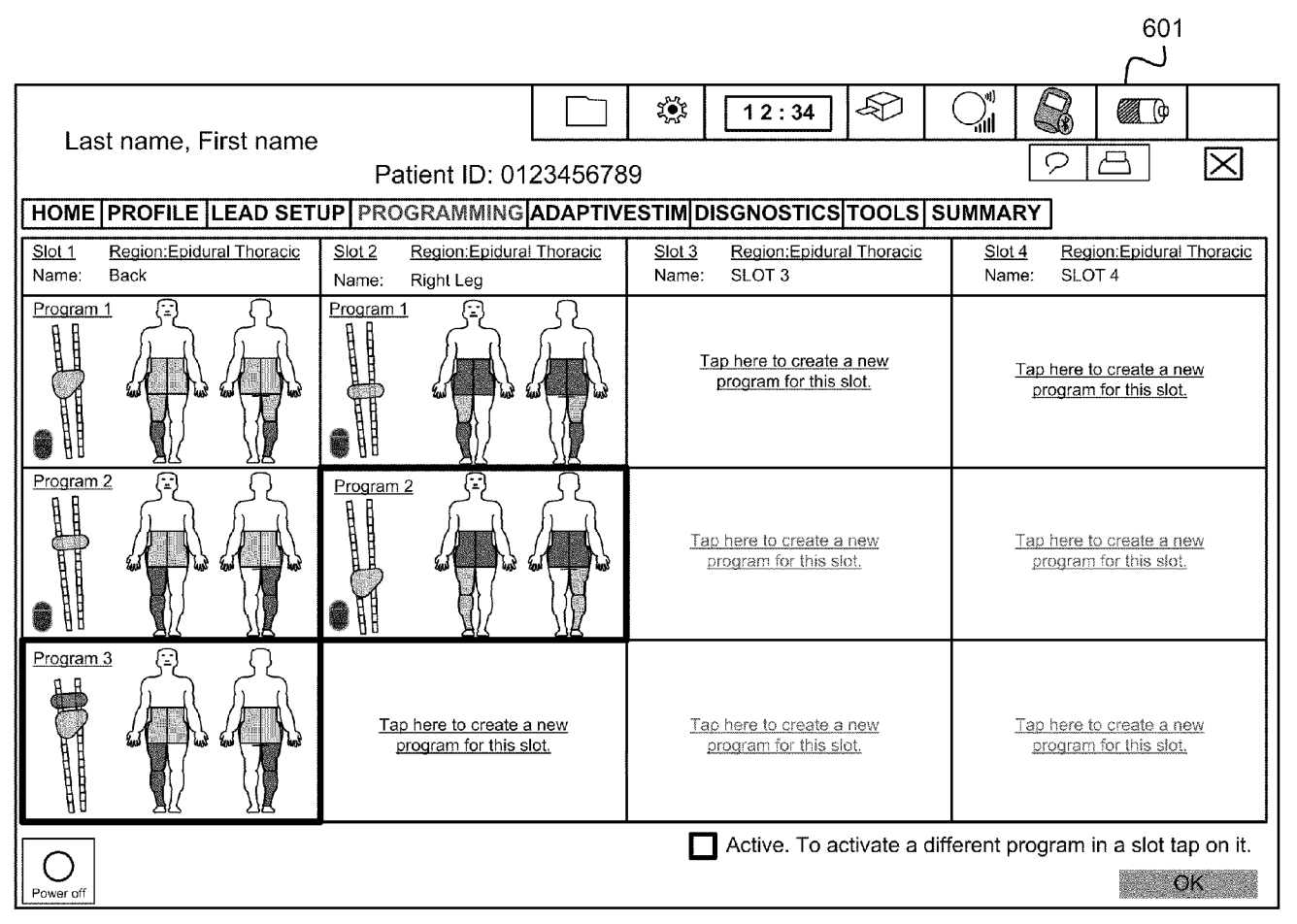

FIG. 6K illustrates a screen shot of the programmer screen 601, where the user may select the add program button 605 under the current slot, e.g., back slot. Selecting the add program button 605 may create a second program tab 606 under the current slot. The user may then follow the same steps as for program 1 under the current slot to create program 2. The names of the different programs in a slot may be edited and changed from the default names by the user. In one example, the user may start with the settings selected for program 1, and vary the settings as desired to create a second program. For example, the user may change the stimulation field 625 by moving the boundaries of the field, selecting different electrodes, and/or changing the intensity of the stimulation field.

FIG. 6L illustrates a screen shot of the programmer screen 601, where the user may use the paresthesia map 604 to indicate the therapy target for which the current program, i.e., program 2 under the back slot, may be applied, as described above with reference to FIG. 6I. In one example, one color or pattern may be used to indicate areas of pain on paresthesia map 604, and as the user adds programming parameters and adjusts their values, a second color or pattern may indicate the paresthesia in the areas corresponding to the active stimulation program settings. The overlap area between the pain and the paresthesia areas may be indicated by a third color or pattern.

The user may then add more programs as additional therapy options under the current slot, i.e., back slot, and may also add programs under other slots, for example, the right leg slot, left leg slot, etc. When the user completes adding desired programs, the user may view the slots and the corresponding programs by selecting the "view all" button 619.

FIG. 6M illustrates a screen shot of the programmer screen 601, where the user has selected to view all the slots and corresponding programs associated with the implantable device with which the programmer may be connected. The slots may have default names such as slot 1, slot 2, etc.

In one example, a user may rename the slots according to the therapy target associated with the programs in that slot, for example, back, right leg, left leg, etc., as illustrated in FIG. 6N. Each of the slots may correspond to a therapy target targeted by the therapy options defined by the programs in each slot. The therapy may be defined by the stimulation provided by electrodes of leads implanted in an implant region such that different combinations of electrodes target different therapy targets. In one example, each of the slots in the examples of FIGS. 6 A-6N pertains to a slot for leads implanted in the epidural thoracic implant region, and each slot targets a particular area, e.g., back, right leg, etc. In other examples, each slot may be associated with a different lead or group of leads. For example, slot 1 may control stimulation by leads implanted proximate to the spine, slot 2 may control stimulation by leads implanted in a peripheral area of patient, e.g., proximate to a peripheral nerve or extremity of the patient, and slot 3 may control stimulation by both sets of leads, as an example.

The example of FIGS. 6A-6N illustrates four slots, each with three options or therapy programs. However, it should be understood that other designs may include fewer or more slots with fewer or more options or therapy programs. In another example, a therapy programming system may support a fixed number of therapy programs (e.g., twenty) which may be shared dynamically among slots (e.g. six programs for slot 1, three programs for slot 2, nine programs for slot 3, with the remaining two programs for a fourth slot).

Under each slot, the corresponding programs may be displayed. Accordingly, each column in FIGS. 6M and 6N corresponds to a slot, and the programs within the column are programs within that slot. A user may select a program to see the details of the program, such as, for example, the values of the parameters, the electrodes active for delivery of stimulation, the STIM zone, and the SHIELD zone (when applicable). In one example, for each program a pain/paresthesia map may show the therapy targets targeted by the program, the stimulation field and the shield displayed over a graphical representation of the leads, with the corresponding electrodes highlighted.

For each slot, an indication may be displayed to show which one of the programs under a slot is the active program. From this view illustrated in FIGS. 6M and 6N, a user may be able to change the active program within a slot by simply clicking on the desired program. In one example, more programs may be added to an existing slot or more slots may be added.

A user may add programs by selecting an empty cell under the desired slot ("Tap here to create a new program for this slot"). The user may also select an existing program to make changes to it or delete it. In this example, while only three program cells are shown for each slot, more programs may be defined and displayed for a slot. In one example, the user may copy a program option from one slot to another by clicking and dragging or by using copy/paste controls (not shown). Copying may be limited to other slots that address the same therapy target or have the same associated leads. Such compatibility may be shown via changes in color, highlight, outline, or other graphical means during a copying operation. In other examples, slot options may be stored by the programmer from previous sessions and may be retrievable in this context. Selecting an empty cell may prompt the user to create a new entry or retrieve a historical entry. In one example, a historical entry may be stored by the programmer, stored in the device memory, or may be available from a network resource such as a server.

In an example, after a session during which the slots and corresponding programs have been created and/or modified, the user may download the slots and programs onto IMD 34. The user may use the telemetry module 67 to transfer the information onto IMD 34. During a subsequent session, a user may upload the slots and programs from IMD 34 to further modify the programs and/or slots, or create more programs and/or slots.

In an example, a patient may upload the slots and programs from IMD 34 using patient programmer, e.g., patient programmer 22. The patient programmer may allow the patient to view the slots and programs and to change an active program for a slot by selecting a new program for the slot. The patient programmer may present the patient with a screen similar to that shown in FIG. 6N, except the patient may not be given the option to create new programs or to modify existing programs.

In other examples, the patient programmer may operate in different modes, where different modes give a user different levels of permissions to functionalities and operations of the programmer. For example, the programmer may be set to a basic mode for new patients and less sophisticated patients, who may be provided with limited permissions, e.g., being allowed to change the active program, turn STIM up or down, or turn the therapy on or off. More sophisticated or more technically-savvy patients may be able to operate the programmer in an expert patient mode, for example, being allowed to perform the functionalities available in basic mode, and additionally to being able to perform other functions such as, for example, creating new programs/slots, or modifying existing programs/slots. The patient programmer may be also operable in clinician mode, where, for example, a clinician or physician may have the capability to operate the patient programmer to modify and change programs/slots as described in this disclosure. The operation of an example patient programmer is described in more detail below.

In an example, some of the programs may have posture-specific settings, and may be selected by a user or a patient using a programmer based on the patient's posture. In one example, the posture of the patient may be automatically detected and an active program in a slot having programs for different postures may be automatically changed according to the detected posture, e.g., changed to a different program of the slot that is associated with the detected posture. In another example, the options presented to a patient may be filtered based on the patient's current posture or position, and only those compatible with that posture or position be offered for selection by the system.

Figure 7:
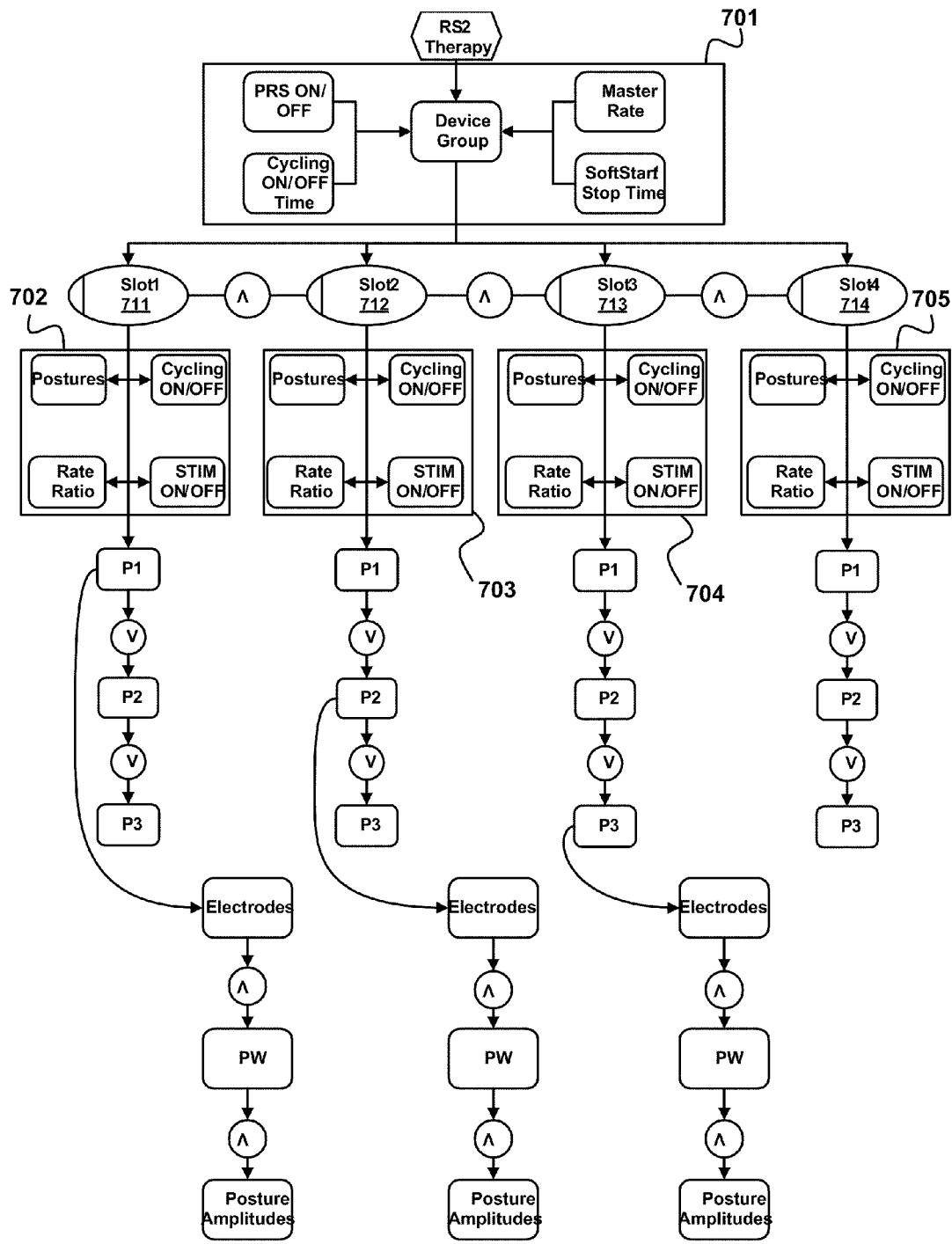
FIG. 7 is a diagram illustrating example configuration options available at each of the program, slot, and device levels, in accordance with this disclosure.

FIG. 7 is a diagram illustrating example configuration options available at each of the program, slot, and device levels, in accordance with this disclosure. A user may use a programmer, e.g., programmer 40, to create therapy programs for a patient to be applied by an implantable medical device, e.g., IMD 34. The programmer may communicate the programs created by the user to the IMD via telemetry modules in both the programmer and the IMD.

The user may utilize a programmer user interface 59 to create and modify programs. The programs may define parameters associated with leads and/or a can placed in or on the patient. The parameters may define stimulation therapy for a therapy target, e.g., lower back, right leg, etc. The user may create or modify programs for different reasons such as, for example, the patient's comfort level, improvement/deterioration of the patient's condition, or the need for different therapies based on different postures.

The user may organize the programs under slots, where each slot corresponds to the therapy target with which the slot programs are associated. For example, a lower back slot may have several programs that target the lower back, and a right leg slot may have several programs that target the right leg. The user may then select one program from each slot, to apply to the corresponding therapy target in the patient. Once the programs and slots are created and/or changed, the user may download them to the IMD, and may activate selected programs. In one example, the patient carrying the IMD may use a patient programmer to access the list of slots and programs and may be able to change the active program for any of the slots. Changing the active program in one slot, may have no influence on the active programs in other slots. In one example, the system may be capable of automatically detecting a posture or activity change and may automatically activate programs associated with the detected postures or activities.

As shown in FIG. 7, the Boolean operators between the different slots correspond to a logical AND indicating that all slots are to be applied to a patient, i.e., therapy is to be applied to the therapy targets associated with all slots. In this example, therapy is to be provided to therapy targets associated with slot 1, slot 2, slot 3, and slot 4. Within each slot, the Boolean operators between the programs that define the therapy options for the therapy target for the slot correspond to a logical OR indicating that one of the several programs should be selected as a therapy option for the slot.

As illustrated in FIG. 7, parameters may be programmed at a device, slot, and program level. The user may use a programmer as described above to program the parameters associated with the IMD and the leads implanted in/on the patient. At the device level 701, the user may define global parameters for the device, where the parameters may be applicable to all programs within all the slots. In this example, some global parameters may be a master rate, PRS on/off, cycling on/off time, and soft start/stop time.

The master rate may be the maximum rate at which the programs may run. For example, the master rate may be 100 Hz, and the rate for each program specified per therapy target may be defined as a fraction of the master rate.

A user may select on or off for PRS on/off to control whether PRS is on or off, e.g., whether amplitude is varied based on detected postures. When PRS is ON, the amplitude is altered when posture change is detected, and when PRS is OFF, the amplitude is the same regardless of posture. Cycling on/off time indicates the length of periods of stimulation and/or the length of periods during which stimulation is not delivered between periods of stimulation. Soft start/stop time indicates the amount of time it takes stimulation to get from 0 to its full amplitude. The user may then create slots corresponding to the different therapy targets for the patient. In this example, there are 4 slots 711, 712, 713, and 714, but there may be more or less, depending on the patient.

Referring to FIG. 7, at the slot level, the user may define slot parameters 702, 703, 704, and 705, which may be applicable to all the programs within the slot. In one example, each slot may correspond to a therapy target (e.g., symptom or pain area), and each set of slots may be associated with a particular device or implant region (e.g., thoracic, subcutaneous, etc.). In this example, some slot parameters may be a list of postures for which the slot is configured, cycling on/off, rate ratio, and STIM on/off.

A user may select on or off for cycling on/off to control whether the cycling feature is on or off. When cycling is on, the cycling on/off times are applied to the stimulations, and when cycling is off, the stimulation is always on. Rate ratio indicates the fraction of the master rate that defines the rate for the programs of the slot. For example, the rate ratio may be ¼, which means the rate for the specific program is ¼ of the master rate, e.g., if the master rate is 100 Hz, then the program rate is 25 Hz. STIM on/off indicates whether stimulation therapy is active or inactive.

Within each slot, a user may create therapy programs that target the therapy target associated with the slot. In this example, each slot has 3 programs, but may have more or less. The user may create programs within the slots and define parameters associated with each program, where the program parameters may be applicable to the associated program. As shown in FIG. 7, the program parameters are connected by a logical AND, indicating that each parameter may need to be specified to define the associated program.

In the example of FIG. 7, some program parameters may be electrodes, pulse width, and posture amplitudes. The electrodes parameter may indicate which electrodes are activated and the current supplied by each activated electrode. Pulse width specifies the width of the pulse of the signal supplied by the electrodes. The posture amplitudes may indicate the pulse amplitude associated with each posture. Each program can have its own amplitude, and may include different amplitudes associated with different postures. According to one example, the upright and lying back postures may be enabled. The upright posture may be associated with a current having an amplitude of 3 mA, and the lying back posture may be associated with an amplitude of 2.4 mA. In such an example, if postures are enabled for the slot, the IMD will deliver stimulation according to the program with a current having an amplitude of 3 mA when the patient is in the upright position, and 2.4 mA when the patient is in the lying back position. Other postural positions may be defined and amplitudes may be associated with each position in a similar manner.

Each posture (standing, sitting, lying down on back, etc.) may have an associated amplitude. When the device senses that the patient changed positions or postures, the associated amplitude is utilized. In this manner, an active program in a given slot may apply different amplitudes for different detected postures. Each posture may be independently enabled for detection and associated with an amplitude or other stimulation parameter value, in some examples. In other words, in some examples, fewer than all postures detectable by the IMD may be associated with a value of the stimulation parameter, e.g., an amplitude.

The user may program the therapy programs based on previous programs associated with the patient, and may make modifications according to the patient's comfort level and/or based on the patient progress and pain level. Once the programs are created, the user may select one program from each slot to activate, for example, program 1 under slot 1, program 2 under slot 2, and program 3 under slot 3. The user may determine subsequently to activate a different program for one of the slots, and the user may use the programmer to access the list of programs and select a new program for one of the slots without affecting the active programs in any of the other slots. For example, the user may decide to activate program 2 under slot 1, instead of program 1, the user may select program 2 under slot 1, which activates that program, and the active programs under slots 2, 3, and 4 remain unaffected by the change under slot 1.

FIGS. 8A-8D illustrate example patient programmer screens, in accordance with this disclosure. In accordance with techniques of this disclosure, a clinician may create and/or modify slots of therapy programs based on therapy targets, as described above. In one example, the clinician may transfer computer-readable instructions defining the programmed therapy from the clinician programmer, e.g., clinician programmer 20, to the patient programmer, e.g., patient programmer 22. In another example, the patient programmer may retrieve the programmed therapy from the IMD after the clinician completes a programming session and transfers the programmed therapy to the IMD. The patient programmer may allow the patient to view the slots and programs and to change an active program for a slot by selecting a new program for the slot.

The patient programmer may give the patient fewer capabilities than those given to a clinician. For example, the patient programmer may limit the patient's ability to create new programs or modify existing programs. In one example, while a clinician may be able to modify all parameters associated with a program and/or a slot, the patient may be able to modify only some parameters. In one example, the patient programmer may have full functionality similar to that available on a clinician programmer. For example, the patient may be able to create new programs, modify existing programs, and add or delete programs using the patient programmer. The modifications, additions, deletions, and new programs created by the patient using the patient programmer may be transferred to the IMD, and at a later time may be also transferred from the IMD to a clinician programmer to ensure all devices are up-to-date and synched. The amount of access and editing/modification capability a patient programmer has may depend on patient expertise and familiarity with the devices and therapies.

In one example, the clinician may determine during programming the permissions a patient has to the patient programmer, and may restrict access to certain functionalities. For example, the patient programmer may be set to a basic mode for new patients and less sophisticated patients, who may be provided with limited permissions, such as permissions to turn the stimulation amplitude up or down, or turn the therapy on or off. More sophisticated or more technically-savvy patients may be able to operate the patient programmer in an expert patient mode, for example, being allowed to perform the functionalities available in basic mode, in addition to being able to control other parameters not available in the basic mode. In one example, expert patient mode may allow the patient to change the active program, change the STIM rate or pulse width, enable and disable cycling or posture response parameters, shift electrode configuration on the leads to create new therapy options, and mark therapy options as less or more efficacious. An expert patient may also have the ability to capture other feedback in a patient diary, mark suspected clinical events in a diagnostic log, cause the device to perform diagnostic tests in a troubleshooting fashion, shift stimulation balance between an anodic case electrode and anodic electrodes on the leads, or schedule therapy changes such that therapy occurrence matches some time-based needs.

Figure 8B:
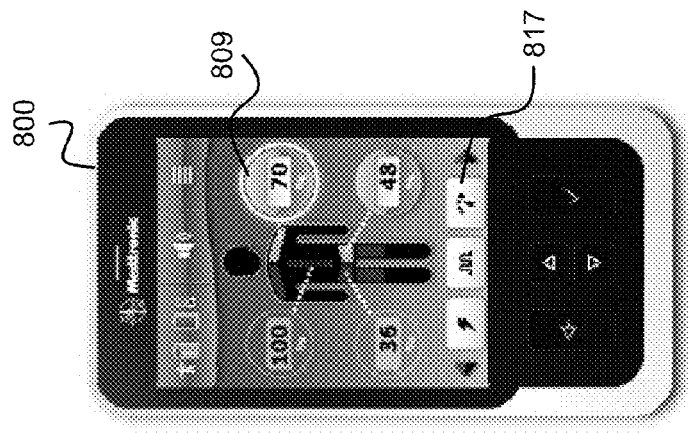
FIGS. 8A-8D illustrate example patient programmer screen shots, in accordance with this disclosure.
Figure 8A:
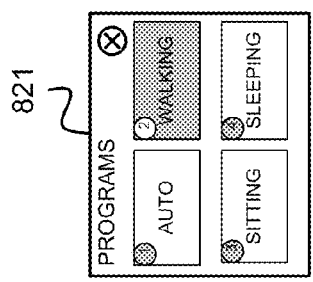
Figure 8A:
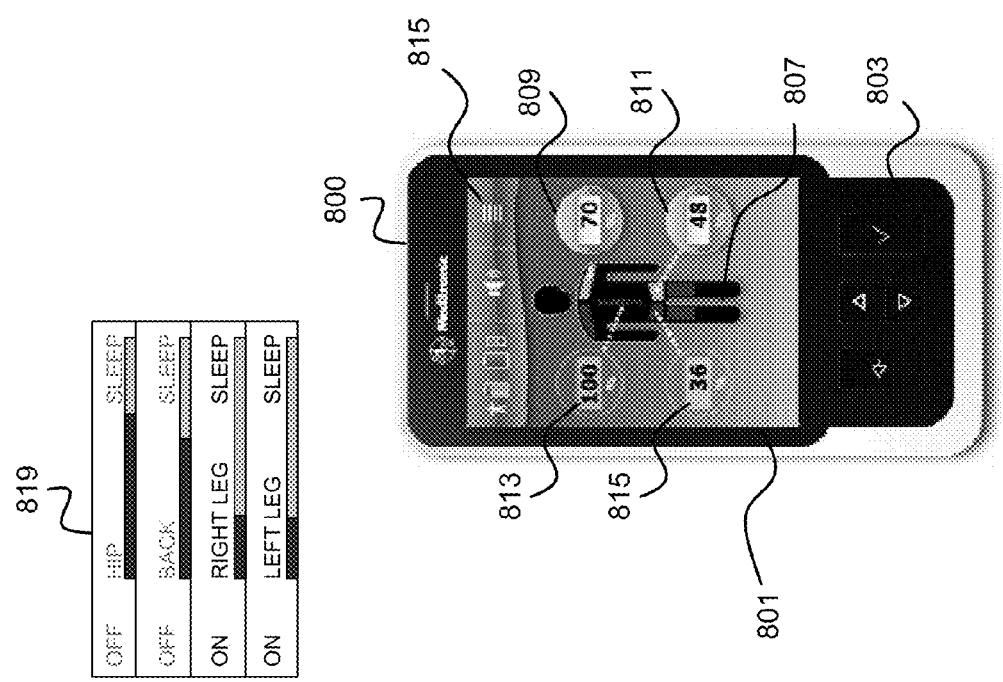

As FIG. 8A illustrates, patient programmer 800 may be a handheld device, with a display 801 and a keypad 803. In one example, display 801 may be a touch-screen display. On an initial screen patient programmer 800 may display general information, for example, date, time, and the like. The display may ask for user input to proceed in operating the device using user input such as, for example, a password or unlocking the display using button combinations. In one example, upon start-up, patient programmer 800 may initiate communication with the IMD via telemetry module 67 (FIG. 4) to retrieve therapy information from the IMD. In another example, upon start-up, patient programmer 800 may display a personalized patient greeting or message, and upon establishing communication with the IMD, patient programmer 800 may display to the patient significant events of interest, e.g., active therapy programs, battery life, and the like.

Patient programmer 800 may display a paresthesia (or dermatomal) map 807, as shown in FIG. 8A. The paresthesia map may correspond to the paresthesia map created on the clinician programmer, as described above. In one example, the clinician programmer may communicate the therapy information, including the paresthesia map, to the IMD. Subsequently, the patient programmer may retrieve therapy information, including the paresthesia map, from the IMD. In another example, the clinician programmer may communicate the therapy information to the patient programmer. In yet another example, the patient programmer may be utilized to create or modify certain therapy programs and options, and later communicate the modifications to the clinician programmer and/or the IMD.

In one example, patient programmer 800 may translate the information retrieved from the IMD into a simplified map for the patient. The maps displayed on the clinician programmer display the paresthesia and pain maps and support an anterior and posterior view of the patient. In this example, the patient programmer may display a simple paresthesia map to limit the amount of information displayed to the patient. In one example, the paresthesia map may be displayed in the upright position regardless of patient's posture. In another example, the paresthesia map may indicate patient's current posture. As described above, during therapy programming, the clinician may name the different slots according to the target area of pain, e.g., right leg, or hip. In one example, the clinician may use the default names, e.g., slot 1, slot 2, etc. The names that the clinician enters for the different slots may be used on patient's programmer.

In one example, the clinician may program different slot names for the patient programmer than those used in the clinician programmer. The slot names may be automatically populated by clinician programmer as a region is selected on the paresthesia map as the therapy target. Similarly, programs within each slot may be named by clinician, by default, or automatically. Where programs correspond to different postures, in some examples, the names of the programs may be based on the posture. In another example, the names of the programs may be based on the time of day when the programs may be activated, e.g., daytime, morning, evening, or night.

The paresthesia map 807 of FIG. 8A may display the different slots and active programs running on the IMD. In this example, there may be 4 slots programmed for this particular patient, although there may be less or more slots, depending on the patient. In this example, the four slots may be represented by bubbles 809, 811, 813, and 815, which may be graphically connected to the corresponding regions on the paresthesia map, e.g., left shoulder, left hip, spine, and right hip, respectively.

Figure 8D:
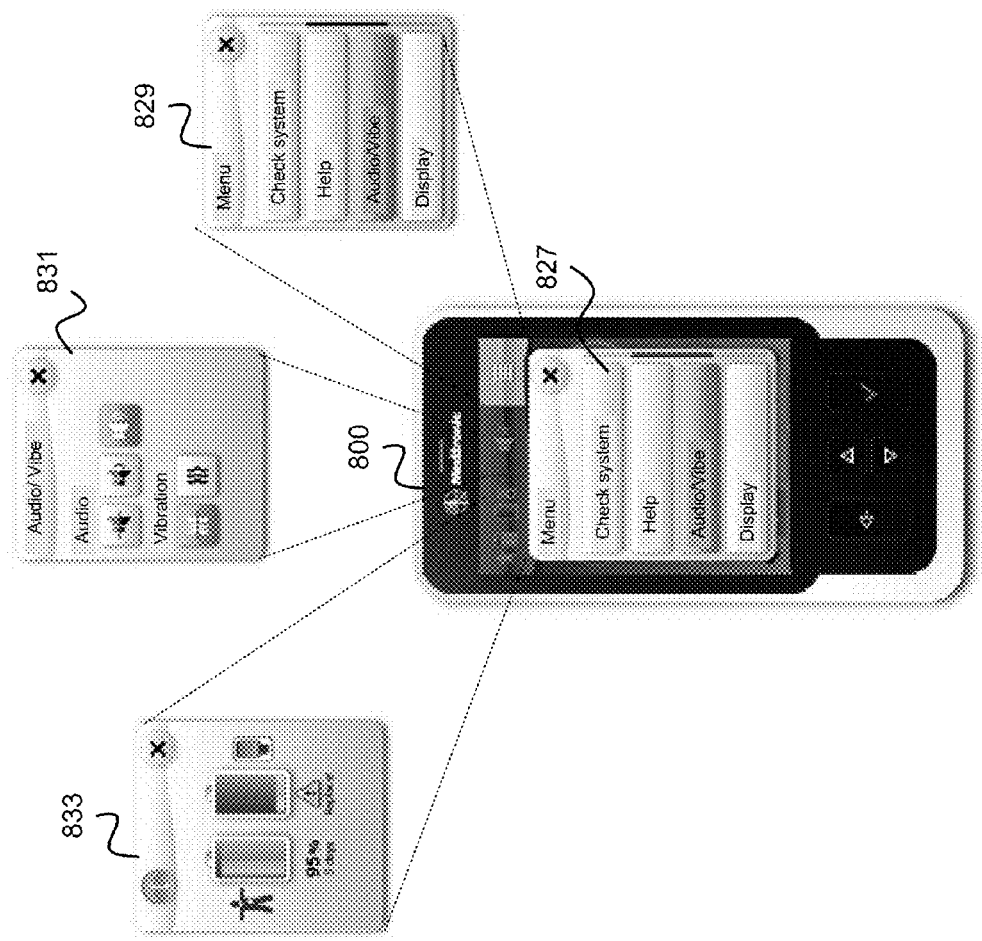
Figure 8C:
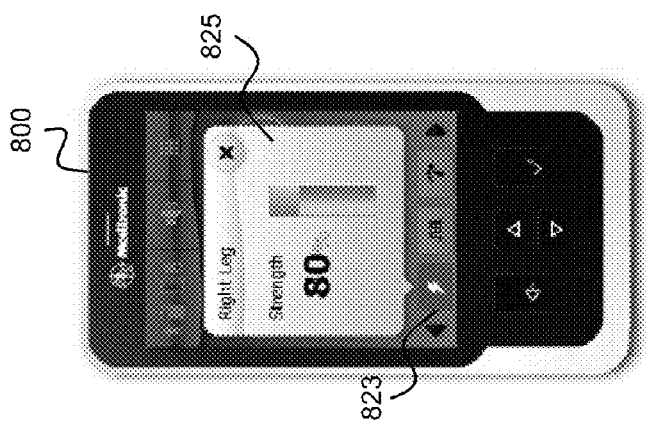

In one example, the clinician may enable therapy associated with some of the slots and disable the other slots. In this example, the slots enabled by the clinician may be represented by bubbles on the display. In this example, the user may be able to turn the stimulation or off for the slots enabled by the clinician. In this example, the STIM is on for the left shoulder slot 809 and the left hip slot 811, and the STIM is off for the right hip slot 815 and the spine slot 813. The slots for which the patient has turned on the STIM may be displayed in a manner indicating to the patient that they are on, and similarly, the slots for which the patient has turned off the STIM may be displayed in a manner indicating that they are off. For example, the STIM ON slots and the corresponding regions on the paresthesia map may be highlighted, as illustrated in FIG. 8C for slots 809 and 811. In another example, the slots for which the patient has turned off the STIM may not be displayed. In one example, the bubbles representing the slots may be populated with an indicator of the active therapy program being delivered to the patient, where the indicator may be, for example, amplitude or intensity of the electrical stimulation.

In one example, patient programmer may present the slots to the patient in a different manner, for example, without using the paresthesia map. In one example, the patient programmer may list the slots on the display as shown in screen shot 819. In this example, the slots may be listed according to the names assigned by the clinician during programming, e.g., according to the therapy targets. As shown in screen shot 819, the list of slots may show all the slots programmed for the patient, whether the slots are ON (e.g., Right Leg Sleep and Left Leg Sleep, indicating the regions and postures) or OFF (e.g., Hip Sleep and Back Sleep, indicating the regions and postures), i.e., STIM is on or off, respectively. The slots for which STIM is ON may be highlighted to indicate to the patient which therapy slots are active, and may also display ON or OFF next to the slot name to further indicate which slots have STIM ON and which have STIM OFF. For each slot, a bar below the name may indicate the relative strength of the stimulation. The indication of the strength of stimulation (e.g., the intensity/amplitude or stimulation current or voltage) may be also displayed numerically, e.g., a percentage of maximum amplitude, a numeric amplitude level, or the like.

In one example, the patient may desire to view details of one of the slots, and adjust parameters that the patient is able to change, i.e., based on permissions indicated by clinician during a programming session. As shown in FIG. 8B, the patient may select, for example, slot 809 to display more details. In one example, the patient may select a slot by tapping once on the bubble representing the slot.

Upon selecting a slot, the slot may be highlighted as illustrated. In one example, when a user selects a slot, a list of items that can be viewed for the selected slot may be displayed for the patient to choose from, as illustrated by the icons 817 displayed in a system tray. Each of the icons may represent a parameter or list of parameters associated with the slot, which patient may view and/or adjust. For example, one icon may be selected to display the therapy programs under the selected slot. The list of programs 821 may show the programs the clinician had programmed for the selected slot, in this example, the four programs corresponding to different postures (e.g., Auto, Walking, Sitting, and Sleeping). In other examples, there may be more or fewer programs. The enabled program may be highlighted as illustrated, e.g., walking. If the patient is given the permission, the patient may select a different active program than the current active one. In other examples, the active program may be automatically selected based on a detected posture or activity of the patient, the time of day, or the activity level of the patient, for example.

In one example, the patient may select other details for viewing for a selected slot. As shown in FIG. 8C, the patient may select icon 823 that is associated with the strength of the active program in the selected slot. Selecting an icon may display the associated details on the display. In this example, the strength of the active therapy program may be displayed as illustrated on display 825 of patient programmer showing the strength of the therapy amplitude, e.g., displaying strength as a relative percentage 80% of the maximum strength for the slot. Other parameter details that patient may view and/or adjust may include strength of program (intensity/amplitude), spread (pulse width), speed (rate), PRS on/off, program selection, cycling (duty cycle), and STIM on/off. In one example, the parameters may be presented to the patient using names that are easier to understand by a patient. For example, the stimulation intensity/amplitude or stimulation current or voltage of a program may be labeled "strength" on the patient programmer, pulse width may be labeled "spread," rate may be labeled "speed," and duty cycle may be labeled "cycling," all terms which may be more meaningful to a patient.

In addition to viewing and/or adjusting parameters for a selected slot, the patient may be able to disable an enabled slot. In one example, the patient may press and hold the representation of the slot on the display to disable it. In some examples, the patient may not be able to enable a disabled slot. In another example, the patient may be able to enable a disabled slot, if it was the patient who disabled the slot, and not the clinician.

In addition to viewing and/or adjusting parameters for a selected slot, the patient may view and/or adjust properties associated with the device. As shown in FIG. 8D, the patient may select from options displayed on top of the patient programmer display. One option may display a menu 829 showing options for the patient from which to select (e.g., Check System, Help, Audio/Vibe, and Display), which allow the patient to perform such actions as, for example, checking the system (e.g., checking operational status, software version, and the like), displaying a help menu, viewing/adjusting audio/vibrating notification options, and adjusting the display. In one example, the notification options may correspond to notifications regarding the programmer such as, for example, low battery, recharge complete, occurrence of an error, detection of an unexpected operation, and the like. In another example, audible and/or vibrational notifications may be utilized to indicate progress and/or status during operations such as, for example, communication with the IMD or the clinician programmer, retrieval of patient information, and the like.

In yet another example, audible and/or vibrational notifications may be utilized to alert the patient to certain events. For example, when adjusting parameters, notifications may alert the patient when a limit has been reached and the parameter may not be adjusted any further. In one example, a system with sensing capabilities may sense when certain events are about to occur, e.g., epileptic seizure, and as a result, utilize notifications to alert the user. In one example, audio notifications may be configured to a variety of levels which may correspond to the severity of the event to which the patient is being alerted, where louder sounds may be used for events with high priority and softer sounds may be used for events with low priority. The patient may also directly select to view/adjust audio/vibrating notification from the display, which displays the appropriate options 831, where the patient can make the desired selection. In one example, when there are multiple events, notifications of the events may be displayed to the patient in order of severity, with the patient receiving notifications of more severe events before notifications associated less severe events. In one example, notifications of events may be also sent to a clinician or a primary physician associated with the patient indicating occurrence of events that may require attention.

In one example, the patient may be also able to select displaying device battery source details 833, which may indicate the amount of battery power remaining and the amount of time remaining. Additionally, the battery details may display a guide for the patient as to the battery level when the battery should be replaced.

Figure 9A:
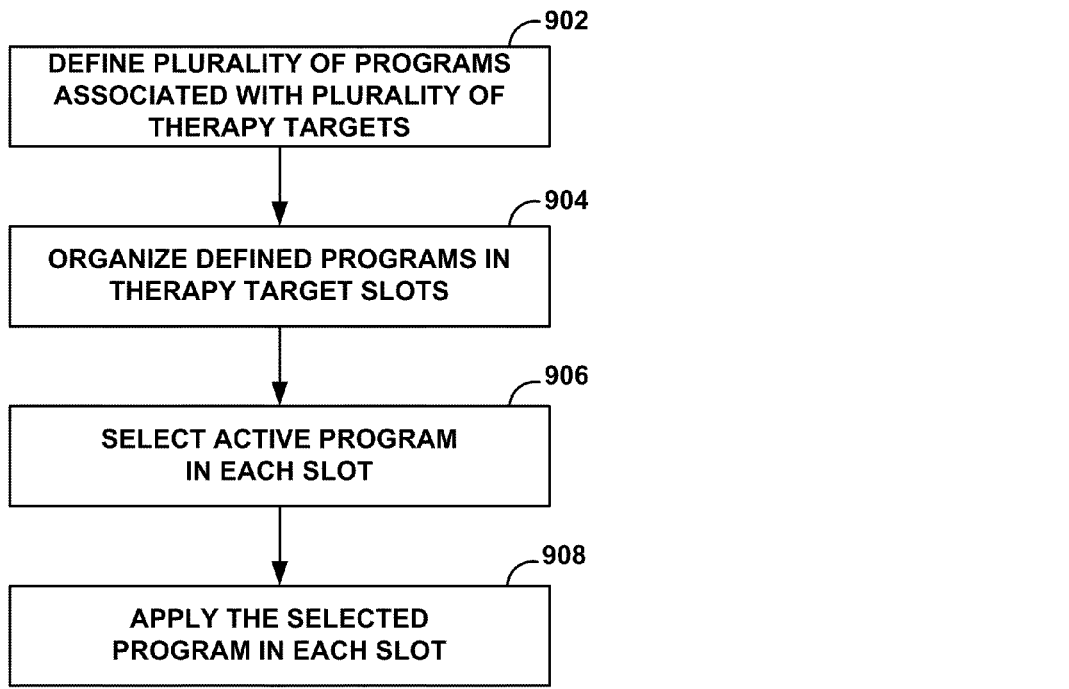
FIG. 9A is a flow diagram illustrating exemplary operation of one or more devices in a system in accordance with aspects of this disclosure.

FIG. 9A is a flow diagram illustrating exemplary operation of one or more devices in a system in accordance with aspects of this disclosure. The one or more devices may be at least one of a programmer (e.g., programmer 40) or an implantable medical device (e.g., IMD 34). A user may utilize the programmer to define different programs associated with different therapy targets in a patient (902). The user may be able to define different parameters associated with each program individually (i.e., program-specific parameters applicable only to the specified program), each therapy target (i.e., parameters applicable to all programs for a given therapy target), and/or all programs (i.e., global parameters applicable to all programs). A processor (e.g., processor 53 or processor 50) may then organize the defined programs (904) in slots according to therapy targets in the patient, where the therapy target may be a symptom or area of pain in the patient. Each slot may include one or more programs, and programs within each slot may vary according to such variables as, for example, posture, activity, level of symptom, or the like. The same or a different processor may then select a program within each slot to activate for the IMD to apply (906), where selection of a program in one slot is independent of selection of a program in another slot. In one example, the selection of programs may be based on user input or may be automated, as described above. In one example, processor 53 in programmer 40 may organize and select the programs, and then communicate the organized and selected programs to IMD 34. In another example, processor 53 of programmer 40 organizes the programs and communicates the organized programs to IMD 34, where processor 50 selects the active programs for the different slots. In yet another example, processor 53 of programmer 40 communicates the defined programs to IMD 34, where processor 50 organizes and selects the programs. IMD 34 may then apply the selected programs in each slot to the patient (908).

Figure 9B:
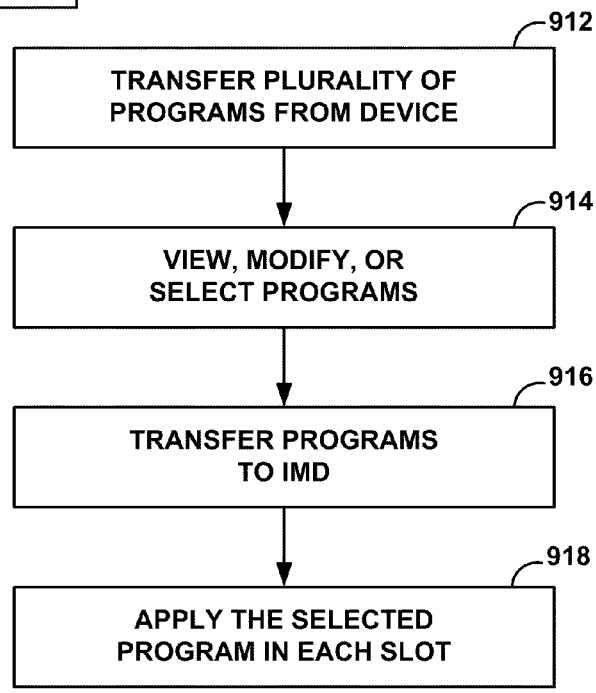
FIG. 9B is a flow diagram illustrating exemplary operation of a programmer in accordance with aspects of this disclosure.

FIG. 9B is a flow diagram illustrating exemplary operation of a programmer in accordance with aspects of this disclosure. In one example, the programmer may be a clinician programmer 20 or a patient programmer 22. A user may utilize the programmer to view, modify, or select different programs associated with a patient. The programmer may communicate with another device to transfer a plurality of stimulation therapy programs (912), where the programs may be associated with one or more therapy targets in the patient. The programs may have been previously defined by a user and organized by therapy target in different slots. The other device may be another programmer or an IMD associated with the patient. In one example, the programmer may be a patient programmer and may retrieve the programs from a clinician programmer or from the IMD. In another example, the programmer may be a clinician programmer and may retrieve the programs from the IMD. The user may then utilize the patient or clinician programmer to view, modify, or select different programs for the therapy targets to apply to the patient (914). Modification or selection of a program associated with one therapy target may be independent of modification or selection of a program associated with another therapy target. In one example, a clinician may retrieve programs from an IMD associated with a patient to modify the therapy programs based on changes to the patient condition or symptoms, for example. In another example, a patient may utilize a patient programmer to retrieve programs from the clinician programmer or from the IMD to view the programs and modify the programs based on the condition of the patient. The patient's ability to view, modify, or select different programs may be limited by the limitation set on the patient programmer as discussed above.

When the user completes modification and/or selection of different programs, the modifications and/or selections, if any, may be transferred to the IMD (916). IMD 34 may then apply the selected programs in each slot to the patient (918), e.g., for delivery of therapy.

While aspects of this disclosure are described in the context of a stimulator as an implantable medical device, techniques described herein may be utilized in other types of medical devices which may be implantable. For example, techniques of the disclosure may be utilized with any type of a neurostimulator, or implantable fluid pumps where an image may show catheter configuration, and where therapy is delivered by pumping fluid such as blood, insulin, pain relief agents, or other medicine to the therapy target.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Many embodiments of the disclosure have been described. Various modifications may be made without departing from the scope of the claims. These and other embodiments are within the scope of the following claims.

The invention claimed is:
1. A method comprising, with one or more processors:
selecting a set of active therapy programs by at least:
selecting a first active therapy program of a first plurality of therapy programs for a first slot, wherein the first slot and the first plurality of therapy programs are associated with a first therapy target in a patient, and wherein the first plurality of therapy programs comprises the first active therapy program and at least one alternative therapy program for the first slot, and
selecting a second active therapy program of a second plurality of therapy programs for a second slot, wherein the second slot and the second plurality of therapy programs are associated with a second therapy target in a patient, and wherein the second plurality of therapy programs comprises the second active therapy program and at least one alternative therapy program for the second slot,
wherein selecting the first active therapy program comprises selecting the first active therapy program independently of selecting the second active therapy program, wherein the set of active therapy programs comprises the first active therapy program and the second active therapy program, and wherein the set of active therapy programs are configured to be applied to the patient; and
defining a first slot parameter for the first slot and a second slot parameter for the second slot, wherein the first slot parameter is applicable to each of the first plurality of therapy programs and the second slot parameter is applicable to each of the second plurality of therapy programs.

2. The method of claim 1, further comprising, with the one or more processors, organizing a plurality of electrical stimulation therapy programs into a plurality of slots, wherein each of the plurality of slots is associated with a therapy target in the patient and wherein at least two therapy programs of the plurality of therapy programs are associated with each of the plurality of slots, wherein the plurality of therapy programs comprises the first plurality of therapy programs and the second plurality of therapy programs.

3. The method of claim 2, further comprising receiving user input, via a user interface, wherein organizing the plurality of electrical stimulation therapy programs into the plurality of slots comprises organizing the plurality of electrical stimulation therapy programs into the plurality of slots based on the user input.

4. The method of claim 1, further comprising transferring, with the one or more processors, a plurality of electrical stimulation therapy programs from a device, wherein the plurality of electrical stimulation therapy programs are organized into a plurality of slots, wherein each of the plurality of slots is associated with a therapy target in the patient and wherein at least two therapy programs of the plurality of therapy programs are associated with each of the plurality of slots, wherein the plurality of therapy programs comprises the first plurality of therapy programs and the second plurality of therapy programs.

5. The method of claim 1, further comprising sensing, via a posture state module, a posture state of the patient, wherein selecting the first active therapy program comprises selecting the first active therapy program based on the posture state of the patient.

6. The method of claim 1, further comprising displaying, via a user interface, a pain map of the patient and a paresthesia map associated with at least one therapy program of the first plurality of therapy programs, wherein displaying the pain map and the paresthesia map comprises overlaying the pain map and the paresthesia map.

7. The method of claim 1, wherein the first active therapy program and the at least one alternative therapy program for the first slot are defined based on at least one of posture, amount of activity of the patient, or intensity of symptoms of the patient.

8. The method of claim 1, wherein the first slot parameter defines at least one of a posture parameter, a cycling parameter, a rate ratio parameter, or a STIM activation parameter.

9. The method of claim 1, wherein selecting the set of active therapy programs further comprises:
selecting a third active therapy program of a third plurality of therapy programs for a third slot, wherein the third slot and the third plurality of therapy programs are associated with a third therapy target in a patient, and wherein the third plurality of therapy programs comprises the third active therapy program and at least one alternative therapy program for the third slot, and
selecting a fourth active therapy program of a fourth plurality of therapy programs for a fourth slot, wherein the fourth slot and the fourth plurality of therapy programs are associated with a fourth therapy target in a patient, and wherein the fourth plurality of therapy programs comprises the fourth active therapy program and at least one alternative therapy program for the fourth slot, wherein each of the first, second, third, and fourth therapy targets defines a different target region of the patient.

10. A system comprising:
one or more processors configured to:
select a set of active therapy programs by at least:
selecting a first active therapy program of a first plurality of therapy programs for a first slot, wherein the first slot and the first plurality of therapy programs are associated with a first therapy target in a patient, and wherein the first plurality of therapy programs comprises the first active therapy program and at least one alternative therapy program for the first slot, and
selecting a second active therapy program of a second plurality of therapy programs for a second slot, wherein the second slot and the second plurality of therapy programs are associated with a second therapy target in a patient, and
wherein the second plurality of therapy programs comprises the second active therapy program and at least one alternative therapy program for the second slot, wherein the one or more processors is configured to select the first active therapy program independently of selecting the second active therapy program, wherein the set of active therapy programs comprises the first active therapy program and the second active therapy program, and wherein the set of active therapy programs are configured to be applied to the patient; and
define a first slot parameter for the first slot and a second slot parameter for the second slot, wherein the first slot parameter is applicable to each of the first plurality of therapy programs and the second slot parameter is applicable to each of the second plurality of therapy programs.

11. The system of claim 10, wherein the one or more processors are further configured to organize a plurality of electrical stimulation therapy programs into a plurality of slots, wherein each of the plurality of slots is associated with a therapy target in the patient and wherein at least two therapy programs of the plurality of therapy programs are associated with each of the plurality of slots, wherein the plurality of therapy programs comprises the first plurality of therapy programs and the second plurality of therapy programs.

12. The system of claim 11, further comprising a user interface configured to receive user input, wherein the one or more processors are configured to organize the plurality of electrical stimulation therapy programs into the plurality of slots based on the user input.

13. The system of claim 10, wherein the one or more processors are further configured to transfer a plurality of electrical stimulation therapy programs from a device, wherein the plurality of electrical stimulation therapy programs are organized into a plurality of slots, wherein each of the plurality of slots is associated with a therapy target in the patient and wherein at least two therapy programs of the plurality of therapy programs are associated with each of the plurality of slots, wherein the plurality of therapy programs comprises the first plurality of therapy programs and the second plurality of therapy programs.

14. The system of claim 10, further comprising a posture state module configured to sense a posture state of the patient, wherein the one or more processors are configured to select the first active therapy program based on the posture state of the patient.

15. The system of claim 10, further comprising a user interface configured to display a pain map of the patient and a paresthesia map associated with at least one therapy program of the first plurality of therapy programs, wherein the user interface is configured to display the pain map and the paresthesia map by at least overlaying the pain map and the paresthesia map.

16. The system of claim 10, wherein the first active therapy program and the at least one alternative therapy program for the first slot are defined based on at least one of posture, amount of activity of the patient, or intensity of symptoms of the patient.

17. The system of claim 10, wherein the first slot parameter defines at least one of a posture parameter, a cycling parameter, a rate ratio parameter, or a STIM activation parameter.

18. The system of claim 10, wherein the one or more processors are configured to select the set of active therapy programs by at least:
selecting a third active therapy program of a third plurality of therapy programs for a third slot, wherein the third slot and the third plurality of therapy programs are associated with a third therapy target in a patient, and wherein the third plurality of therapy programs comprises the third active therapy program and at least one alternative therapy program for the third slot, and
selecting a fourth active therapy program of a fourth plurality of therapy programs for a fourth slot, wherein the fourth slot and the fourth plurality of therapy programs are associated with a fourth therapy target in a patient, and wherein the fourth plurality of therapy programs comprises the fourth active therapy program and at least one alternative therapy program for the fourth slot,
wherein each of the first, second, third, and fourth therapy targets defines a different target region of the patient.

19. The system of claim 10, further comprising an external programmer comprising the one or more processors.

20. The system of claim 10, further comprising an implantable electrical stimulator comprising the one or more processors.

21. A system comprising:
means for selecting a set of active therapy programs by at least:
selecting a first active therapy program of a first plurality of therapy programs for a first slot, wherein the first slot and the first plurality of therapy programs are associated with a first therapy target in a patient, and wherein the first plurality of therapy programs comprises the first active therapy program and at least one alternative therapy program for the first slot, and
selecting a second active therapy program of a second plurality of therapy programs for a second slot, wherein the second slot and the second plurality of therapy programs are associated with a second therapy target in a patient, and wherein the second plurality of therapy programs comprises the second active therapy program and at least one alternative therapy program for the second slot,
wherein the means for selecting selects the first active therapy program independently of selecting the second active therapy program, wherein the set of active therapy programs comprises the first active therapy program and the second active therapy program, and wherein the set of active therapy programs are configured to be applied to the patient; and
means for defining a first slot parameter for the first slot and a second slot parameter for the second slot, wherein the first slot parameter is applicable to each of the first plurality of therapy programs and the second slot parameter is applicable to each of the second plurality of therapy programs.

22. The system of claim 21, further comprising means for organizing a plurality of electrical stimulation therapy programs into a plurality of slots, wherein each of the plurality of slots is associated with a therapy target in the patient and wherein at least two therapy programs of the plurality of therapy programs are associated with each of the plurality of slots, wherein the plurality of therapy programs comprises the first plurality of therapy programs and the second plurality of therapy programs.

23. The system of claim 22, further comprising means for receiving user input, wherein the means for organizing organizes the plurality of electrical stimulation therapy programs into the plurality of slots based on the user input.

24. The system of claim 21, further comprising means for transferring a plurality of electrical stimulation therapy programs from a device, wherein the plurality of electrical stimulation therapy programs are organized into a plurality of slots, wherein each of the plurality of slots is associated with a therapy target in the patient and wherein at least two therapy programs of the plurality of therapy programs are associated with each of the plurality of slots, wherein the plurality of therapy programs comprises the first plurality of therapy programs and the second plurality of therapy programs.

25. The system of claim 21, further comprising means for sensing a posture state of the patient, wherein the means for selecting selects the first active therapy program based on the posture state of the patient.

26. The system of claim 21, further comprising means for displaying a pain map of the patient and a paresthesia map associated with at least one therapy program of the first plurality of therapy programs, wherein the means for displaying displays the pain map and the paresthesia map by at least overlaying the pain map and the paresthesia map.

27. The system of claim 21, wherein the first active therapy program and the at least one alternative therapy program for the first slot are defined based on at least one of posture, amount of activity of the patient, or intensity of symptoms of the patient.

28. The system of claim 21, wherein the first slot parameter defines at least one of a posture parameter, a cycling parameter, a rate ratio parameter, or a STIM activation parameter.

29. The system of claim 21, wherein the means for selecting a set of active therapy programs selects the set of active therapy programs by at least:
selecting a third active therapy program of a third plurality of therapy programs for a third slot, wherein the third slot and the third plurality of therapy programs are associated with a third therapy target in a patient, and wherein the third plurality of therapy programs comprises the third active therapy program and at least one alternative therapy program for the third slot; and
selecting a fourth active therapy program of a fourth plurality of therapy programs for a fourth slot, wherein the fourth slot and the fourth plurality of therapy programs are associated with a fourth therapy target in a patient, and wherein the fourth plurality of therapy programs comprises the fourth active therapy program and at least one alternative therapy program for the fourth slot,
wherein each of the first, second, third, and fourth therapy targets defines a different target region of the patient.

30. A computer-readable storage medium comprising instructions that cause a programmable processor to:
select a set of active therapy programs by at least:
selecting a first active therapy program of a first plurality of therapy programs for a first slot, wherein the first slot and the first plurality of therapy programs are associated with a first therapy target in a patient, and wherein the first plurality of therapy programs comprises the first active therapy program and at least one alternative therapy program for the first slot, and selecting a second active therapy program of a second plurality of therapy programs for a second slot, wherein the second slot and the second plurality of therapy programs are associated with a second therapy target in a patient, and wherein the second plurality of therapy programs comprises the second active therapy program and at least one alternative therapy program for the second slot, wherein the instructions cause the programmable processor to select the first active therapy program independently of selecting the second active therapy program, wherein the set of active therapy programs comprises the first active therapy program and the second active therapy program, and wherein the set of active therapy programs are configured to be applied to the patient; and define a first slot parameter for the first slot and a second slot parameter for the second slot, wherein the first slot parameter is applicable to each of the first plurality of therapy programs and the second slot parameter is applicable to each of the second plurality of therapy programs.

31. The computer-readable storage medium of claim 30, further comprising instructions that cause the programmable processor to organize a plurality of electrical stimulation therapy programs into a plurality of slots, wherein each of the plurality of slots is associated with a therapy target in the patient and wherein at least two therapy programs of the plurality of therapy programs are associated with each of the plurality of slots, wherein the plurality of therapy programs comprises the first plurality of therapy programs and the second plurality of therapy programs.

32. The computer-readable storage medium of claim 31, wherein the instructions cause the programmable processor to organize the plurality of electrical stimulation therapy programs into the plurality of slots based on user input.

33. The computer-readable storage medium of claim 30, further comprising instructions that cause the programmable processor to transfer a plurality of electrical stimulation therapy programs from a device, wherein the plurality of electrical stimulation therapy programs are organized into a plurality of slots, wherein each of the plurality of slots is associated with a therapy target in the patient and wherein at least two therapy programs of the plurality of therapy programs are associated with each of the plurality of slots, wherein the plurality of therapy programs comprises the first plurality of therapy programs and the second plurality of therapy programs.

34. The computer-readable storage medium of claim 30, wherein the instructions cause the programmable processor to select the first active therapy program based on a sensed posture of the patient.

35. The computer-readable storage medium of claim 30, further comprising instructions that cause the programmable processor to display a pain map of the patient and a paresthesia map associated with at least one therapy program of the first plurality of therapy programs, wherein the instructions cause the programmable processor to display the pain map and the paresthesia map by at least overlaying the pain map and the paresthesia map.

36. The computer-readable storage medium of claim 30, wherein the first active therapy program and the at least one alternative therapy program for the first slot are defined based on at least one of posture, amount of activity of the patient, or intensity of symptoms of the patient.

37. The computer-readable storage medium of claim 30, wherein the first slot parameter defines at least one of a posture parameter, a cycling parameter, a rate ratio parameter, or a STIM activation parameter.

38. The computer-readable storage medium of claim 30, wherein the instructions that cause the programmable processor to select the set of active therapy programs further comprise instructions that cause the programmable processor to:

select a third active therapy program of a third plurality of therapy programs for a third slot, wherein the third slot and the third plurality of therapy programs are associated with a third therapy target in a patient, and wherein the third plurality of therapy programs comprises the third active therapy program and at least one alternative therapy program for the third slot, and select a fourth active therapy program of a fourth plurality of therapy programs for a fourth slot, wherein the fourth slot and the fourth plurality of therapy programs are associated with a fourth therapy target in a patient, and wherein the fourth plurality of therapy programs comprises the fourth active therapy program and at least one alternative therapy program for the fourth slot, wherein each of the first, second, third, and fourth therapy targets defines a different target region of the patient.

* * * * *